United States Patent
Li et al.

(10) Patent No.: US 11,992,688 B2
(45) Date of Patent: May 28, 2024

(54) INTRACARDIAC ENERGY HARVESTING DEVICE AND IMPLANTABLE ELECTRONIC MEDICAL DEVICE

(71) Applicants: Wei Hua, Beijing (CN); Zhou Li, Beijing (CN)

(72) Inventors: Zhou Li, Beijing (CN); Wei Hua, Beijing (CN); Zhuo Liu, Beijing (CN); Yiran Hu, Beijing (CN); Han Ouyang, Beijing (CN)

(73) Assignees: Wei Hua, Beijing (CN); Zhou Li, Beijing (CN)

( * ) Notice: Subject to any disclaimer, the term of this patent is extended or adjusted under 35 U.S.C. 154(b) by 5 days.

(21) Appl. No.: 17/917,925

(22) PCT Filed: May 26, 2020

(86) PCT No.: PCT/CN2020/092367
§ 371 (c)(1),
(2) Date: Oct. 8, 2022

(87) PCT Pub. No.: WO2021/203533
PCT Pub. Date: Oct. 14, 2021

(65) Prior Publication Data
US 2023/0149720 A1 May 18, 2023

(30) Foreign Application Priority Data
Apr. 9, 2020 (CN) .......................... 202010274659.1

(51) Int. Cl.
*A61N 1/378* (2006.01)
*A61N 1/37* (2006.01)
*A61N 1/375* (2006.01)

(52) U.S. Cl.
CPC ............... *A61N 1/37* (2013.01); *A61N 1/375* (2013.01); *A61N 1/3785* (2013.01)

(58) Field of Classification Search
CPC ........................................................ H02N 1/04
See application file for complete search history.

(56) References Cited

U.S. PATENT DOCUMENTS

| 5,941,904 A * | 8/1999 | Johnston ............ A61N 1/36542 |
|---|---|---|
| | | 607/19 |
| 8,135,469 B2 * | 3/2012 | Roberts ................ H02K 7/1876 |
| | | 607/35 |

(Continued)

FOREIGN PATENT DOCUMENTS

| CN | 105071685 A | 11/2015 |
| CN | 107961441 A | 4/2018 |
| CN | 108310649 A | 7/2018 |

*Primary Examiner* — Eric D. Bertram

(57) ABSTRACT

An intracardiac energy harvesting device includes a shell; a fixing mechanism arranged on the shell, and a fixing mechanism configured to fix the shell to an interior of a heart chamber to enable the shell to move along with beating of heart; wherein a nanogenerator module is packaged in the shell, which is configured to output electric energy in response to movement of the shell along with the heart beat; and a power management module is packaged in the shell for managing electric energy output by the nanogenerator module. According to the intracardiac energy collecting device disclosed by the present invention, the biological mechanical energy generated by heart beating can be collected in the heart through a minimally invasive interventional operation mode, surgical wounds are small, damage to the heart cannot be caused, and infection can be effectively avoided.

20 Claims, 22 Drawing Sheets

(56) References Cited

U.S. PATENT DOCUMENTS

| | | | | |
|---|---|---|---|---|
| 8,217,523 B2* | 7/2012 | Brown | ............... | F03G 5/062 290/1 R |
| 8,311,632 B2* | 11/2012 | Pless | ............... | A61N 1/3785 607/35 |
| 9,014,818 B2* | 4/2015 | Deterre | ............... | A61N 1/3975 607/116 |
| 2004/0222637 A1* | 11/2004 | Bednyak | ............... | F03B 13/20 290/1 R |
| 2005/0027332 A1* | 2/2005 | Avrahami | ............... | A61N 1/3785 607/61 |
| 2005/0256549 A1* | 11/2005 | Holzer | ............... | H02K 35/02 607/35 |
| 2006/0184206 A1* | 8/2006 | Baker, III | ............... | H02K 35/06 607/35 |
| 2007/0156053 A1* | 7/2007 | Ferek-Petric | ............... | A61N 1/36514 600/508 |
| 2007/0276444 A1* | 11/2007 | Gelbart | ............... | A61N 1/3785 607/6 |
| 2007/0293904 A1* | 12/2007 | Gelbart | ............... | A61N 1/3785 607/35 |
| 2009/0171404 A1* | 7/2009 | Irani | ............... | A61N 1/056 290/1 R |
| 2009/0171408 A1* | 7/2009 | Solem | ............... | A61B 5/1107 607/35 |
| 2012/0059389 A1* | 3/2012 | Larson | ............... | G16H 40/67 607/116 |
| 2012/0290043 A1* | 11/2012 | Gross | ............... | A61N 1/3785 607/48 |
| 2014/0243848 A1* | 8/2014 | Auricchio | ............... | A61N 1/37205 607/32 |
| 2019/0028040 A1* | 1/2019 | Song | ............... | H02N 1/04 |
| 2019/0381324 A1* | 12/2019 | Wang | ............... | A61N 1/36007 |
| 2020/0147398 A1* | 5/2020 | Park | ............... | H02N 2/186 |

\* cited by examiner

INTRACARDIAC ENERGY HARVESTING DEVICE AND IMPLANTABLE ELECTRONIC MEDICAL DEVICE

BACKGROUND OF THE PRESENT INVENTION

Field of Invention

The present invention relates to the field of medical instruments, in particular to an intracardiac energy harvesting device and an implantable electronic medical device.

Description of Related Arts

With the continuous development of medical technology, the increasing number of miniature implantable electronic medical devices meeting various disease diagnosis and detection can be met. Implantable pulse generators such as cardiac pacemaker, brain pacemaker and the like are widely used in the field of medical diagnosis and treatment. However, almost all implantable medical devices are powered by an energy storage medium such as a battery, and the lithium battery is used as a current most mature power supply to be applied to clinic, but still has a non-avoidance defect-battery capacity, so that the service life of the implantable electronic medical device is affected; and when the electric quantity of the storage medium is reduced and the implanted medical device cannot work normally or stops working, the life health of the patient is seriously harmed. At present, the problems are mainly solved through periodic device replacement procedures, which not only needs expensive medical expenses, but also needs to bear large surgical risks.

In order to solve the problem, in the prior art, some biological mechanical energy of the surface of a biological organ is acquired through an energy harvesting technology, and the biological mechanical energy is converted into electric energy to realize the self-energizing mode of the electronic device. For example, a piezoelectric nanogenerator with a nano-piezoelectric material or a surface of a biological organ such as a diaphragm and a heart is attached to the surface of a biological organ such as a diaphragm and a heart through a sliding triboelectric nanogenerator, so that the nano-piezoelectric material is deformed, or the two friction layers of the sliding triboelectric nanogenerator are relatively sliding, so that electric energy is converted into electric energy.

In the process of implementing the embodiment of the present invention, the inventor finds at least the following defects in the prior art:

A piezoelectric nanogenerator or a sliding triboelectric nanogenerator and the like are adopted to collect biological mechanical energy on the surface of the biological organ. The biological mechanical energy collection mode is adopted in the surface of the heart. In clinical practice, power generation components such as the piezoelectric nanogenerator or the sliding triboelectric nanogenerator need to be sewn and attached to the pericardial outer membrane, so that the normal physiological function of the heart can be influenced by the damage of the piezoelectric nanogenerator or the sliding triboelectric nanogenerator, and the piezoelectric nanogenerator or the sliding triboelectric nanogenerator and other power generation components need to be connected with external electronic medical devices such as a pulse emitter through a wire, so that the infection probability is increased. Therefore, the method for collecting the biological mechanical energy on the surface of the biological organ needs to be implanted through a large incision operation, the clinical application has great difficulty, the damage to the organism is large, and the method does not have an actual application prospect.

In addition, the cardiac pacemaker currently applied clinically consists of a pacing lead implanted in the heart and a pulse generator buried under the chest of the chest, pulse current is generated through the pulse generator, the pulse generator is conducted to the heart through the pacing lead, and the pulse generator buried under the chest of the chest is used for driving or guiding the surface of the organ or tissue such as the heart, the diaphragm muscle, the lung and the like to collect the biological mechanical energy, that is, the harvesting part is relatively fixed, so that the structure or material of the power generation part is improved, and the problem is avoided.

SUMMARY OF THE PRESENT INVENTION

The main purpose of the embodiment of the present invention is to provide an intracardiac energy harvesting device and an implantable electronic medical device, so as to solve the technical problem that in the prior art, a large wound operation needs to be adopted to implant a power generation unit on the surface of a heart to cause damage to the heart and easy infection of the organism in the prior art.

In order to achieve the above object, according to one aspect of the present invention, an intracardiac energy harvesting device is provided, comprising: a fixing mechanism arranged on the shell, which is configured to fix the shell to an interior of a heart chamber to enable the shell to move along with beating of heart; a nanogenerator module packaged in the shell, which is configured to output electrical energy in response to movement of the shell as the heart beats; and a power management module packaged in the shell, which is used for managing the electric energy output by the nanogenerator module.

According to another aspect of the present invention, an intracardiac energy harvesting device implantation method is provided, wherein the above intracardiac energy harvesting device is adopted. The implantation method comprises steps of: implanting the intracardiac energy harvesting device into a heart chamber by an interventional procedure; and fixing the intracardiac energy harvesting device on a cardiac tissue by a fixing mechanism.

According to yet another aspect of the present invention, an implantable electronic medical device is provided, which comprises: an intracardiac energy harvesting device; and a load functional unit electrically connected to an output end of a power management module of the intracardiac energy harvesting device, wherein the intracardiac energy harvesting device is configured to provide electrical energy for the load function unit.

The one or more technical solutions provided in the embodiments of the present invention at least have the following technical effects or advantages:

According to the intracardiac energy collecting device provided by the present invention, the nanogenerator module and the power management module are packaged in the shell, and a fixing mechanism is arranged on the shell to form an energy collecting device in the heart. The device is suitable for being implanted into the heart chamber through the interventional operation, so that the intracardiac energy collecting device can be implanted into the heart to collect the biological mechanical energy generated by heart beating, the surgical trauma is small, damage to the heart cannot be caused, and infection can be effectively avoided. Therefore, the technical problem that in the prior art, an implantable electronic medical device is self-powered, a large wound operation needs to be adopted to implant a power generation unit on the surface of the heart, so that the heart is damaged and the organism is prone to infection is solved.

Due to the adoption of the fixing mechanism, the shell is fixed in the heart chamber, and the inner energy collecting device is driven to move integrally through contraction and relaxation of the heart, so that the internal nanogenerator module can be converted into electric energy in response to the movement and output to the power management module for management, the technical problem of limited bottleneck-battery life of the implantable electronic medical device can be achieved, the technical problem that the existing implantable electronic medical device energy supply technology bottleneck-battery life is limited and the existing cardiac pacemaker with the electrode wire and the capsule bag is large in size and low in integration degree can be solved, and continuous diagnosis and treatment can be achieved through minimally invasive surgery implantation.

According to the intracardiac energy harvesting device provided by the present invention, the nanogenerator module and the power management module are packaged in the shell, and a fixing mechanism is arranged on the shell to form an energy collecting device in the heart. The device adopts the device with the size and shape suitable for being implanted into the heart chamber through the interventional operation, the overall quality is light, the structure is centralized, energy collection can be realized, normal physiological functions of the heart are not affected, and the burden on the heart is small.

DETAILED DESCRIPTION OF THE PREFERRED EMBODIMENT

Figure 1:
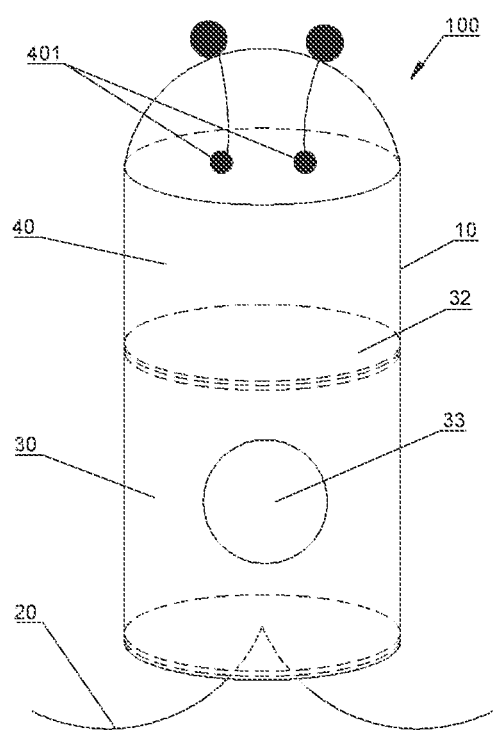
FIG. 1 is a perspective view of an intracardiac energy harvesting device, in accordance with some embodiments.

It should be noted that the embodiments in the present application and the features in the embodiments can be combined with each other without conflict. The present invention will be described in detail below with reference to the accompanying drawings and in combination with the embodiments.

It should be noted that, unless otherwise specified, all technical and scientific terms used in the present application have the same meaning as commonly understood by one of ordinary skill in the art to which this application belongs.

In the present invention, the terms such as "upper and lower" used in the present invention are generally in the direction shown in the drawings, or for vertical, vertical or gravity directions; for ease of understanding and description, "left and right" are generally left and right as shown in the drawings; "inner and outer" refers to the inner and outer sides of the contour relative to each component itself, but the above-mentioned words are not intended to limit the present invention.

In addition, descriptions relating to "first", "second" and the like in the present disclosure are for descriptive purposes only and are not to be construed as indicating or implying relative importance or implicitly indicating the number of indicated technical features. Thus, features defined with "first" and "second" may explicitly or implicitly include at least one of the features. In the description of the present invention, "a plurality of" means at least two, for example, two, three, and the like, unless specifically defined otherwise.

When used herein, the term "and/or" includes any and all combinations of one or more of the associated listed items. Expressions such as "at least one of" when preceding a list of elements modifies the entire list of elements rather than modifying individual elements in the column. In order to solve the technical problem in the prior art that an implantable electronic medical device is self-powered, a large wound operation needs to be adopted to implant a power generation unit on the surface of a heart, so that the heart is damaged and the organism is easy to infect, and the present invention provides an intracardiac energy harvesting device and an implantable electronic medical device.

The present invention is further described below with reference to the accompanying drawings.

Embodiment 1

The present embodiment provides an intracardiac energy harvesting device 100 having a size and shape adapted to be implanted into the interior of a heart chamber by an interventional procedure, the intracardiac energy harvesting device 100 being applied to collecting biological mechanical energy generated by heart beating by an interventional procedure implanted inside the heart chamber. The interventional surgery is an interventional procedure in medicine, is a minimally invasive treatment by using modern science and technology means, can introduce a specially-made catheter, guide wire and other precise instruments into a human body under the guidance of medical image equipment, and performs diagnosis and local treatment on pathological conditions in the body. For example, the intracardiac energy harvesting device 100 can be implanted into the heart chamber through a catheter through a femoral vein puncture.

Figure 2:
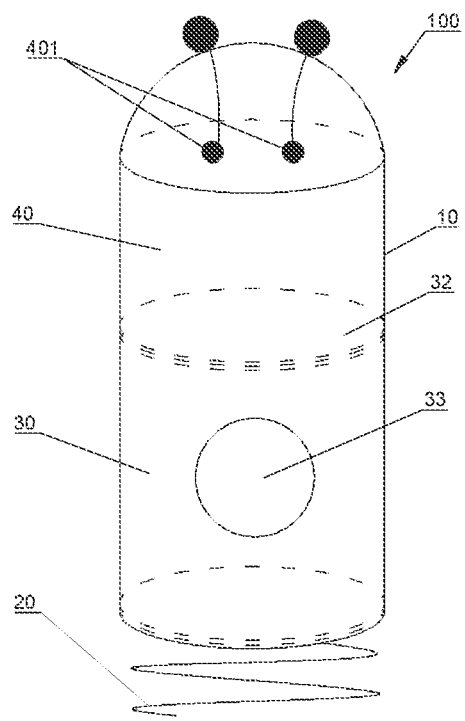
FIG. 2 is a perspective view of an intracardiac energy harvesting device having a helical fixation mechanism modified from FIG. 1.
Figure 3:
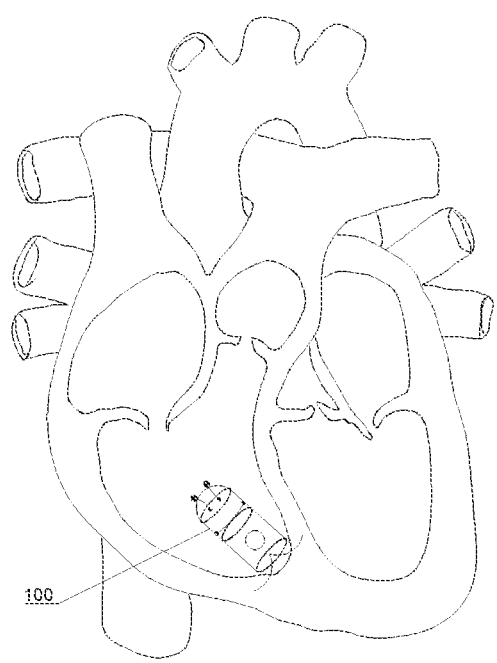
FIG. 3 is a working schematic diagram of the intracardiac energy harvesting device in FIG. 1 being fixed inside a heart chamber.

FIG. 1 is a perspective view of an intracardiac energy harvesting device 100, in accordance with some embodiments. FIG. 2 is a perspective view of an intracardiac energy harvesting device having a helical fixation mechanism modified from FIG. 1. FIG. 3 is a working schematic diagram of the intracardiac energy harvesting device in FIG. 1 being fixed inside the heart chamber.

Referring to FIG. 1 to FIG. 3, an intracardiac energy harvesting device 100 includes a shell 10, a fixing mechanism 20, a nanogenerator module 30, and a power management module 40.

The shell 10 is an internally hollow packaging shell for encapsulating the nanogenerator module 30 (or the nanogenerator module 30 and the power management module 40) therein, so as to prevent external influence on the nanogenerator module 30 (or the nanogenerator module 30 and the power management module 40), and provide a placement environment for the nanogenerator module 30 (or the nanogenerator module 30 and the power management module 40).

The shell 10 may be exposed to the interior of the heart chamber as a shell 10 in contact with blood in the intracardiac energy harvesting apparatus 100, so that the shell 10 may include an insulating material with good biocompatibility and good blood compatibility, for example, the shell 10 may include at least one of polylactic acid, polyvinyl alcohol, polytetrafluoroethylene, rubber and a composite material. The shell can be processed and formed by 3D printing or infusion using a mold.

An outer diameter of the shell 10 is 5 mm-15 mm, and a length of the shell 10 is 1 cm-5 cm. Within this size range, the shell 10 can be adapted to be implanted inside the heart chamber by means of an interventional procedure, and can be appropriately movable inside the heart chamber, so that the shell 10 can move in the heart chamber as the heart beats. Preferably, the outer diameter of the shell 10 is 7-10 mm, the length of the shell 10 is 2 cm-3 cm, and the energy harvesting device 100 in the heart has a smaller volume.

The shell 10 has a cylindrical shape, a prism shape, and an irregular cylindrical or prismatic shape (for example, one end is an arc surface, and one end thereof is a cylindrical or prismatic shape with an arc surface), but is not limited thereto, so that the shell 10 can have a small size in the radial direction (the width direction) and have a relatively small size in the axial direction (the length direction), so that the shell 10 can have a smaller size in the radial direction (the width direction) and have a certain volume in the radial direction (the width direction) to encapsulate the nanogenerator module 30 and the power management module 40, thereby not affecting the output of the nanogenerator module 30. Preferably, the shell 10 is cylindrical. If the outer shell 10 is spherical, the outer diameter of the spherical shell can only be below 7 mm due to interventional operation implantation, so that the size of the spherical shell is small, and the output of the nanogenerator module 30 is not facilitated. Of course, the shell 10 may also be in other shapes other than the cylindrical shape.

The fixing mechanism 20 is disposed on the shell 10, the fixing mechanism 20 may be fixed to the outside of the shell 10, and the fixing mechanism 20 is configured to fix the shell 10 inside the heart chamber to enable the shell 10 to move along with the beating of the heart. After the intracardiac energy harvesting device 100 is implanted inside the heart chamber by means of an interventional procedure, the shell 10 is fixed inside the heart chamber by means of the fixing mechanism 20, for example, may be fixed on an endocardial and/or myocardial layer of the heart. When the heart beats, the energy harvesting device 100 in the heart can be driven to move, so that the nanogenerator module 30 can convert the electric energy into electric energy and transmit the electric energy to the power management module 40 in response to the movement.

The securing mechanism 20 may be disposed at an end or side of the shell 10. Preferably, the fixing mechanism 20 is disposed at the end of the shell 10, so that one end of the shell 10 in the length direction thereof is connected to the inner wall of the heart, so that the shell 10 is adapted to the internal space shape of the heart chamber without affecting the contraction and relaxation of the heart, but also facilitates the movement of the shell 10 along the length direction of the shell 10 along with the contraction and relaxation of the heart, thereby facilitating the output of the nanogenerator module 30.

The heart inner energy collecting device 100 can be fixed to the inner wall of the left ventricle of the heart through the fixing mechanism 20, the position close to the heart tip is fixed to the position, the relative fluctuation amplitude and intensity of the heart are larger, the motion amplitude and intensity of the energy collecting device 100 in the heart are larger, and therefore the output of the nanogenerator module 30 is facilitated. Of course, the fixed position of the intra-cardiac energy harvesting device 100 in the heart chamber is not limited thereto.

The fixing mechanism 20 is selected form a group consisting of a claw-shaped fixing mechanism, a hook-shaped fixing mechanism, a spiral fixing mechanism and a screw fixing mechanism, but is not limited thereto. Based on the motivation, a person skilled in the art may further adopt other structures of fixing mechanisms. FIG. 1 shows an example of a fixing mechanism 20 using a claw-shaped fixing mechanism, and FIG. 2 shows an example of using a spiral fixing mechanism for the fixing mechanism 20.

The nanogenerator module 30 is packaged in the shell 10, and the nanogenerator module 30 is configured to output electrical energy in response to the movement of the shell 10 with the heart beat, that is, the nanogenerator module 30 can convert the motion of the shell 10 with the heart beat into electrical energy. The length of the nanogenerator module 30 is 0.5 cm to 4.5 cm. Preferably, the length of the nanogenerator module 30 is 1.5 cm.

Figure 4:
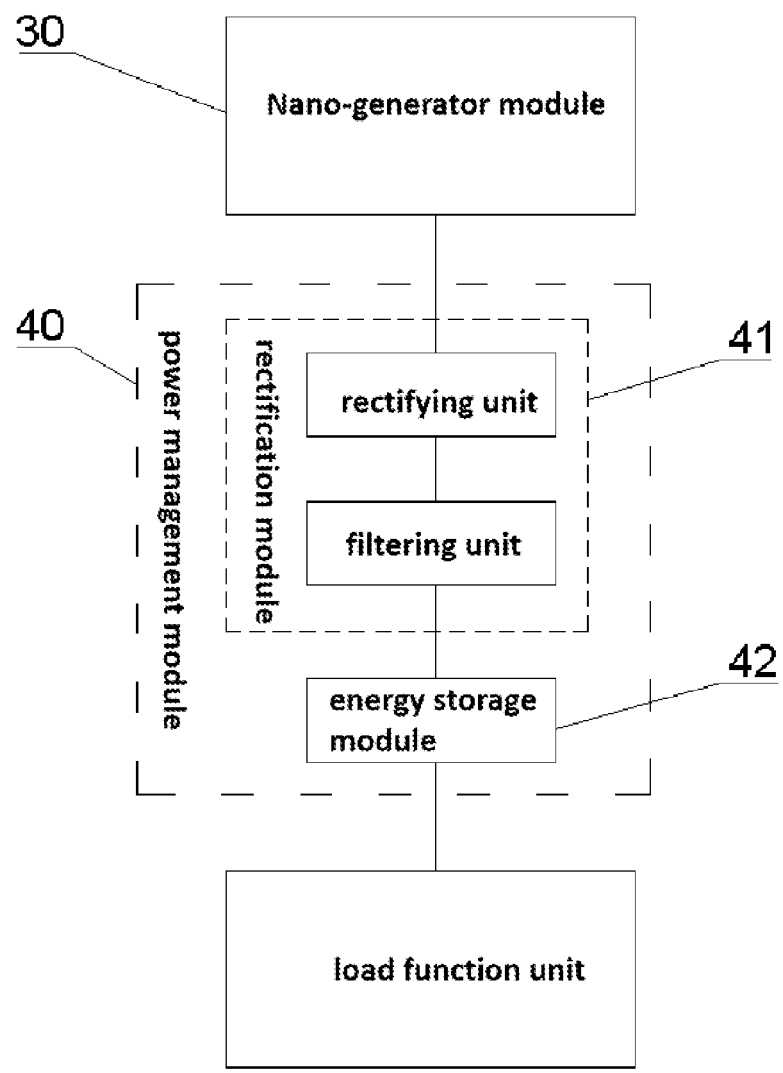
FIG. 4 is a schematic diagram of a functional module of the intracardiac energy harvesting device according to some embodiments.

The power management module 40 may be packaged in the shell 10, but is not limited thereto, and optionally, the power management module 40 may be separately packaged outside the shell 10 by means of a packaging material. The power management module 40 is used for managing the electric energy output by the nanogenerator module 30. When both the power management module 40 and the nanogenerator module 30 are packaged in the shell 10, the overall integration level of the energy harvesting device 100 in the heart can be improved. The power management module 40 may comprise a rectification module 41 and an energy storage module 42, wherein the rectification module 41 is used for converting the alternating current output by the nanogenerator module 30 into a direct current, and the energy storage module 42 is used for storing the direct current output by the rectification module 41. The rectifying module 41 may include a rectifying unit and a filtering unit. The rectifying unit converts the alternating current output by the nanogenerator module 30 into a direct current. For example, a rectifier bridge may be used. The filtering unit converts the pulsating direct current output by the rectifying unit into a relatively stable direct current, and provides the direct current to the energy storage module 42 for storage, for example, the energy storage module 42 may be a rechargeable lithium battery or an energy storage capacitor. The energy storage module 42 may provide electrical energy to a load functional unit, etc., of the implantable electronic medical device for operation thereof. In the interior of the shell 10, the power management module 40 and the nanogenerator module 30 may be spaced apart by a hard layer, and an output electrode of the nanogenerator module 30 may be electrically connected to an input electrode of the rectifying unit of the power management module 40 by means of a flexible circuit board or a wire. The power output electrode 401 of the power management module 40 can extend to the outside of the shell 10 through a wire to provide electrical energy for the load. The power management module 40 has a length of 0.5 cm to 4.5 cm. Preferably, the length of the power management module 40 is 1 cm. The relative positions of the nanogenerator module 30 and the power management module 40 in the shell 10 are not limited, for example, the nanogenerator module 30 may be located at one end of the shell 10 away from the fixing mechanism 20, and the nanogenerator module 30 may also be located at one end, close to the fixing mechanism 20, in the shell 10. FIG. 4 is a schematic diagram of a functional module of an energy harvesting device in a heart.

Figure 5:
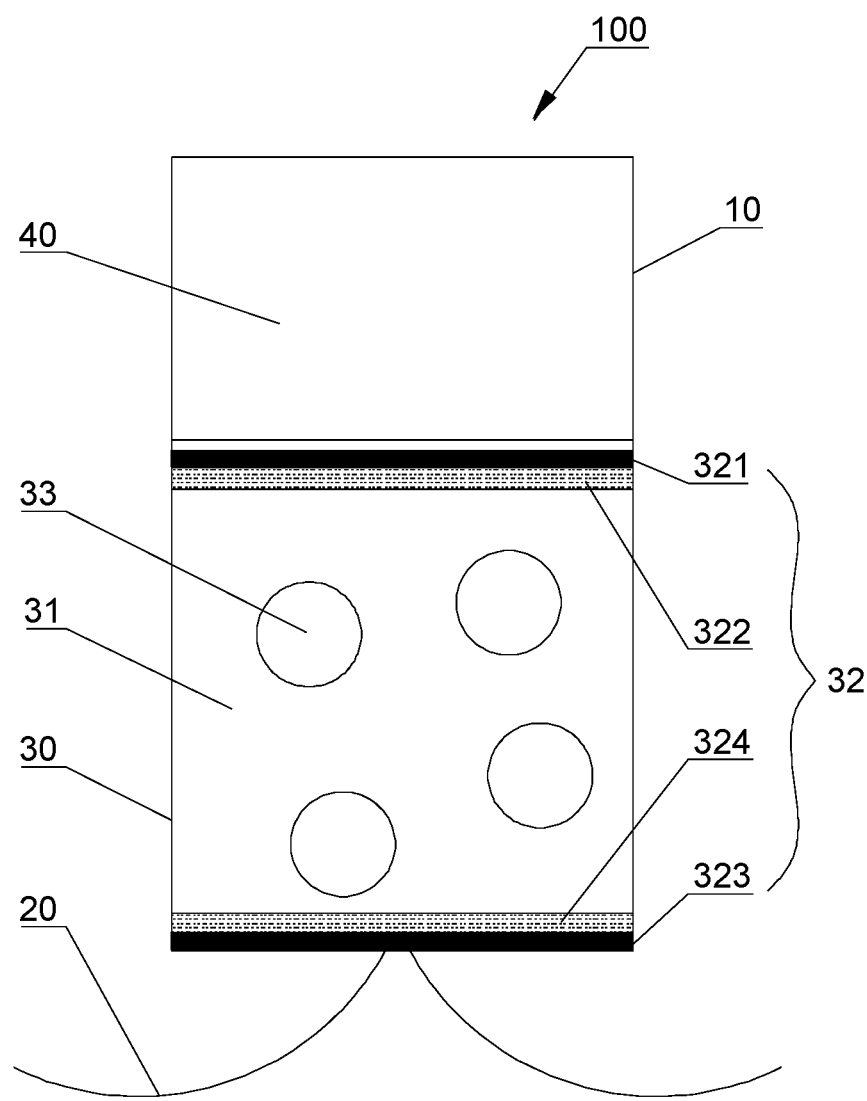
FIG. 5 is a schematic structural diagram of an intracardiac energy harvesting device according to some embodiments.

FIG. 5 is a schematic structural diagram of an intracardiac energy harvesting device according to some embodiments.

Referring to FIG. 5, in the present embodiment, the nanogenerator module 30 includes a first cavity 31, at least one power generation unit 32, and at least one first runout body 33.

The first cavity 31 is a cavity inside the shell 10.

The at least one power generation unit 32 is disposed in the first cavity 31, and the power generation unit 32 may be disposed on at least one of the top wall, the bottom wall and the side wall of the first cavity 31. The at least one power generation unit 32 is selected from a group consisting of a triboelectric nanogenerator unit and a triboelectric nanogenerator.

At least one of the first runout bodies 33 is freely movably disposed in the first cavity 31, that is, when the heart beats and drives the shell 10 to move through the fixing mechanism 20, the shell 10 drives the first runout body 33 to move in the first cavity 31. The first runout body 33 is configured to move in the first cavity 31 and make contact with and/or impact the power generation unit 32 in response to the beating of the heart (i.e., contraction and contraction of the heart), so that the power generation unit 32 outputs an electrical signal to the power management module 40. The first runout body 33 can be integrally formed, and can also be a multi-layer combined runout body.

Figure 6:
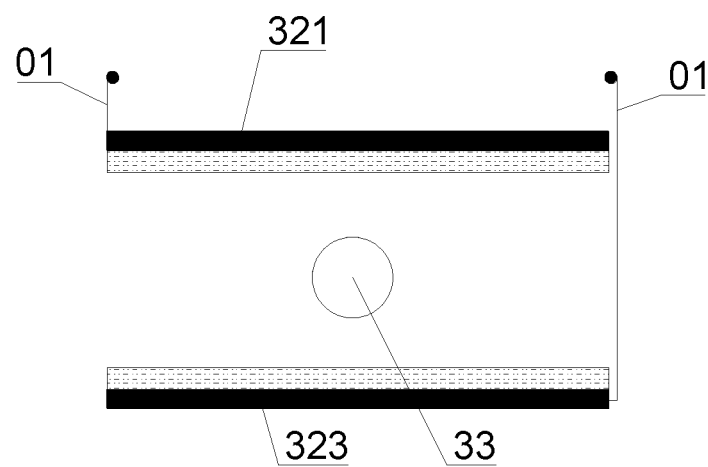
FIG. 6 is a schematic structural diagram of a power generation unit in FIG. 5.

FIG. 6 is a schematic structural diagram of the power generation unit 32 in FIG. 5.

Referring to FIG. 5 and FIG. 6, in the present embodiment, the power generation unit 32 is a triboelectric nanogenerator unit, and the power generation unit 32 comprises a first electrode layer 321, a first friction layer 322, a second electrode layer 323, and a second friction layer 324 disposed in contact with the second electrode layer 323.

The first runout body 33 is configured to move between the first friction layer 322 and the second friction layer 324 in response to the beating of the heart, so that the first runout body 33 is in contact with and separated from the first friction layer 322, and the first runout body 33 is in contact with and separated from the second friction layer 324, so that the first electrode layer 321 and the second electrode layer 323 output electrical signals to the power management module 40. The first electrode layer 321 and the second electrode layer 323 may be electrically connected to an input electrode of the rectifying unit of the power management module 40 through the first wire 01, respectively. The first friction layer 322 and the second friction layer 324 are arranged face to face, and refer to both the first friction layer 322 and the second friction layer 324 being located between the first electrode layer 321 and the second electrode layer 323.

There is a difference between the material of the first friction layer 322 and the material of the outer surface of the first runout body 33, so that a contact charge can be generated on the surfaces of the first runout body 33 and the first friction layer 322 in a contact or friction process, and the surface of one of the first runout body 33 and the first friction layer 322 is positively charged, and the other surface is negatively charged; the material of the second friction layer 324 is different from the material of the outer surface of the first runout body 33, so that contact charges can be generated on the surfaces of the first runout body 33 and the second friction layer 324 in a contact or friction process, the surface of one of the first runout body 33 and the second friction layer 324 is positively charged, and the other surface is negatively charged.

Each of the first friction layer 322, the second friction layer 324 and the first runout body 33 is selected from a group consisting of an insulator material, a semiconductor material, and a conductor material. The conventional insulating material has triboelectric characteristics, and can be used as a material for preparing the first friction layer 322, the second friction layer 324 and the first runout body 33. Compared with the insulator, the semiconductor and the metal all have frictional electrical properties that are prone to loss of electrons, and therefore, the semiconductor and the metal can also be used as materials for preparing the first friction layer 322, the second friction layer 324 and the first runout body 33. In this embodiment, each of the first friction layer 322, the second friction layer 324 and the first runout body 33 are selected from a group consisting of polyethylene, polypropylene, polystyrene, silica gel, polydimethylsiloxane, polyester, polyurethane, polymethacrylate, polytetrafluoroethylene and nylon, polyimide, nitrile rubber, fluororubber, latex, chitin, cellulose, gold, silver, copper, aluminum, iron and an alloy material, but is not limited thereto. Preferably, both the first friction layer 322 and the second friction layer 324 are polytetrafluoroethylene, and the first runout body 33 is polypropylene.

Each of the material of the first electrode layer 321 and the material of the second electrode layer 323 is selected from a group consisting of a metal and a conductive polymer material, wherein the metal is selected from a group consisting of gold, silver, copper, aluminum, iron and an alloy, and the conductive polymer material is selected from a group consisting of carbon nanotubes, graphene and carbon black, but is not limited thereto. Preferably, the material of the first electrode layer 321 and the material of the second electrode layer 323 are both gold. The first electrode layer 321 and the second electrode layer 323 may be coated on the surface of the corresponding friction layer by magnetron sputtering, but are not limited thereto, and the first electrode layer 321 and the second electrode layer 323 may be prepared in other manners.

By using the power generation unit 32 of the structure, when the heart beats to drive the shell 10 to move, the first runout body 33 reciprocates between the first friction layer 322 and the second friction layer 324, so that a potential difference is generated between the first friction layer 322 and the second friction layer 324. Under the coupling of the friction power and the electrostatic induction effect, the first electrode layer 321 and the second electrode layer 323 generate an electric potential difference, and the alternating electrical signal will continue to be generated in the external circuit, so that the first electrode layer 321 and the second electrode layer 323 continuously output an electrical signal to the power management module 40.

The power generation layer formed by the first electrode layer 321 and the first friction layer 322 is symmetrically arranged with the power generation layer formed by the second electrode layer 323 and the second friction layer 324, and the materials of the first friction layer 322 and the second friction layer 324 are the same.

The first friction layer 322 or the second friction layer 324 may be prepared by replacing an insulating material or a semiconductor material with a conductor material, that is, the first friction layer 322 may be a conductor material, and instead of the first electrode layer 321 in contact therewith, the second friction layer 324 may be a conductor material, and instead of the second electrode layer 323 in contact therewith, the structure of the power generation unit 32 can be simplified, and the manufacturing cost is reduced. The conductor material may be selected from at least one of a metal, a conductive oxide, and a conductive polymer material.

At least one of the contact surfaces of the first friction layer 322, the contact surface of the second friction layer 324, and the outer surface of the first runout body 33 is selected from a group consisting of a micro-nano structure, a dot conjugate of the nanomaterial, and a coating of the nanomaterial. The micro-nano structure comprises microstructures on the order of micron or submicron. The microstructure is selected form a group consisting of nanowires, nanotubes, nanoparticles, nano-trenches, micro-trenches, nano-cones, micrometer cones, nanospheres, and microspherical structures, but is not limited thereto. A contact surface of the first friction layer 322 faces a surface of the second friction layer 324, and a contact surface of the second friction layer 324 faces a surface of the first friction layer 322. By adopting the arrangement, the contact area between the contact surface of the first friction layer 322 and the outer surface of the first runout body 33 can be increased, so that the contact charge amount is increased, the contact area between the contact surface of the second friction layer 324 and the outer surface of the first runout body 33 can be increased, the contact charge amount is increased, and then the electrical signal output of the first electrode layer 321 and the first electrode layer 321 is facilitated.

The first electrode layer 321 and the second electrode layer 323 of the power generation unit 32 are sequentially arranged along the length direction of the shell 10. In this arrangement, when the shell 10 is fixed to the inner wall of the heart along its length direction and moves along the length direction of the shell 10, the first runout body 33 moves in the first cavity 31 along the length direction of the shell 10, and reciprocates between the first friction layer 322 and the second friction layer 324, thereby facilitating the output of electrical signals between the first electrode layer 321 and the first electrode layer 321. In this case, the fixing mechanism 20 may be disposed at an end of the shell 10 along the length direction of the shell 10. When there is only one power generation unit 32 in the first cavity 31, the first electrode layer 321 and the second electrode layer 323 can be respectively fixed to the top wall and the bottom wall of the first cavity 31 in the length direction of the shell 10.

It should be noted that the position of the first electrode layer 321 and the second electrode layer 323 of the power generation unit 32 in the shell 10 is not limited thereto. Optionally, the first electrode layer 321 and the second electrode layer 323 of the power generation unit 32 are sequentially arranged along the width direction of the shell 10. In this case, the fixing mechanism 20 may be disposed at the side of the shell 10 along the width direction of the shell 10. When there is only one power generation unit 32 in the first cavity 31, the first electrode layer 321 and the second electrode layer 323 can be respectively fixed on the side wall of the first cavity 31 along the length direction of the shell 10.

The first runout body 33 has an outer diameter of 100 μm-5 mm, but is not limited thereto, which facilitates free movement of the first runout body 33 in the first cavity 31. Preferably, the outer diameter of the first runout body 33 is 2 mm.

Two or more first runout bodies 33 can be arranged in the space formed between the first friction layer 322 and the second friction layer 324, for example, the plurality of first runout bodies 33 can be arranged under the condition that the overall quality of the energy harvesting device 100 in the heart does not affect the normal work of the heart, and the output performance of the power generation unit 32 can be improved.

The first runout body 33 may be any one of a polyhedron, a cylinder, a sphere and an ellipsoid, but is not limited thereto.

Figure 7:
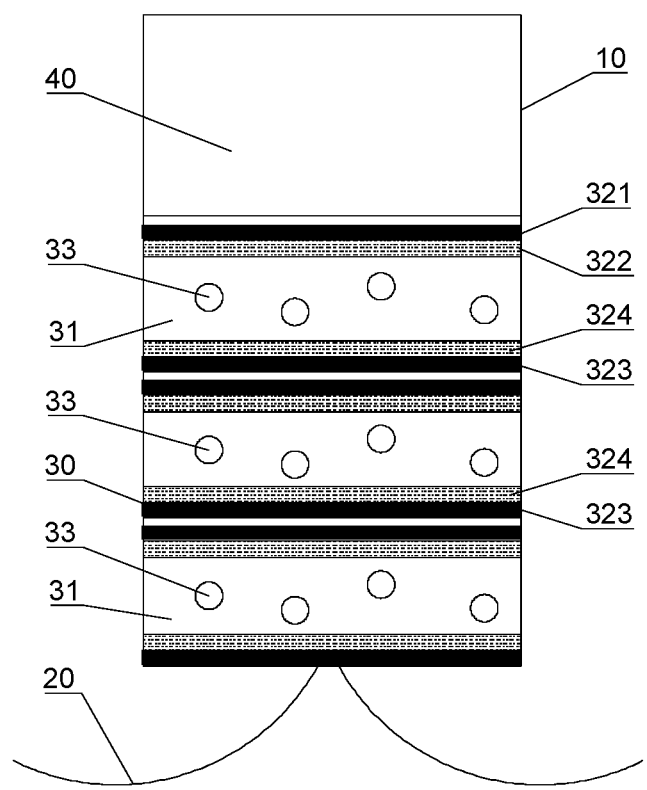
FIG. 7 is a schematic structural diagram of an intracardiac energy harvesting device having a plurality of power generation units modified from FIG. 1.
Figure 8:
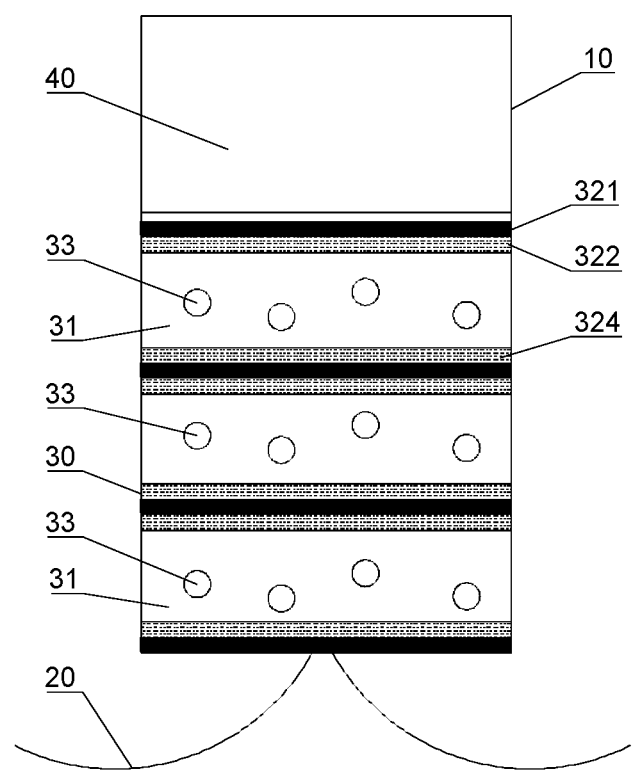
FIG. 8 is a schematic structural diagram of an intracardiac energy harvesting device having a plurality of power generation units modified from FIG. 1.

FIG. 7 is a schematic structural diagram of an intracardiac energy harvesting device having a plurality of power generation units modified from FIG. 1. FIG. 8 is a schematic structural diagram of an intracardiac energy harvesting device having a plurality of power generation units modified from FIG. 1.

Referring to FIG. 7 and FIG. 8, the number of the power generation units 32 may be multiple, the plurality of power generation units 32 are stacked, and each of the space formed between the first friction layer 322 and the second friction layer 324 of each power generation unit 32 moves in respective corresponding spaces, so as to make contact and separation between the first friction layer 322 and the second friction layer 324 of the respective power generation units 32, so that the first electrode layer 321 and the second electrode layer 323 of each power generation unit 32 output electrical signals to the power management module 40. The number of the power generation units 32 may be 2-10, preferably, the number of the power generation units 32 is 3. By adopting the arrangement, the current output performance of the nanogenerator module 30 can be effectively improved.

The plurality of power generation units 32 are sequentially stacked along the length direction of the shell 10, and the first electrode layer 321 and the second electrode layer 323 of each power generation unit 32 are sequentially arranged along the length direction of the shell 10. The above arrangement is used to facilitate the placement of the plurality of power generation units 32 in the shell 10.

The power management module 40 may include at least one rectification unit corresponding to the number of power generation units 32, each power generation unit 32 is connected to a rectifying unit, and the output ends of all the rectifying units are connected in parallel. By adopting the arrangement, the overall current output of the nanogenerator module 30 can be improved.

The two adjacent power generation units 32 can be separated by a separation layer, so that each power generation unit 32 is connected in parallel after respective rectification after each power generation unit 32 is subjected to power generation. The electrode layer of the power generation unit 32 is disposed on the inner wall of the first cavity 31 or the separation layer. FIG. 7 shows an example of a plurality of power generation units 32 separated by a separation layer between two adjacent power generation units 32. It should be noted that the two adjacent power generation units 32 can share the same electrode layer, and each electrode layer is coupled together through a diode, so that when the potential distribution between any two electrode layers changes, current output can be formed in the external circuit. FIG. 8 shows an example of a plurality of power generation units 32 sharing the same electrode layer between two adjacent power generation units 32.

Embodiment 2

The present embodiment provides an intracardiac energy harvesting device 100 having a size and shape adapted to be implanted into the interior of a heart chamber by an interventional procedure. The intracardiac energy harvesting device 100 comprises a shell 10, a fixing mechanism 20, a nanogenerator module 30, and a power management module 40.

The nanogenerator module 30 comprises a first cavity 31, at least one power generation unit 32, and at least one first runout body 33.

The first cavity 31 is a cavity inside the shell 10.

The at least one power generation unit 32 is disposed in the first cavity 31, and the power generation unit 32 may be disposed on at least one of the top wall, the bottom wall and the side wall of the first cavity 31. The at least one power generation unit 32 is selected from a group consisting of a triboelectric nanogenerator unit and a triboelectric nanogenerator.

At least one of the first runout bodies 33 is freely movably disposed in the first cavity 31, that is, when the heart beats and drives the shell 10 to move through the fixing mechanism 20, the shell 10 drives the first runout body 33 to move in the first cavity 31. The first runout body 33 is configured to move in the first cavity 31 and make contact with and/or impact the power generation unit 32 in response to the beating of the heart (i.e., contraction and contraction of the heart), so that the power generation unit 32 outputs an electrical signal to the power management module 40. The first runout body 33 can be integrally formed, and can also be a multi-layer combined runout body.

In embodiment 1, the power generation unit 32 includes a first electrode layer 321, a first friction layer 322 disposed in contact with the first electrode layer 321, a second electrode layer 323, and a second friction layer 324 disposed in contact with the second electrode layer 323.

Figure 9:
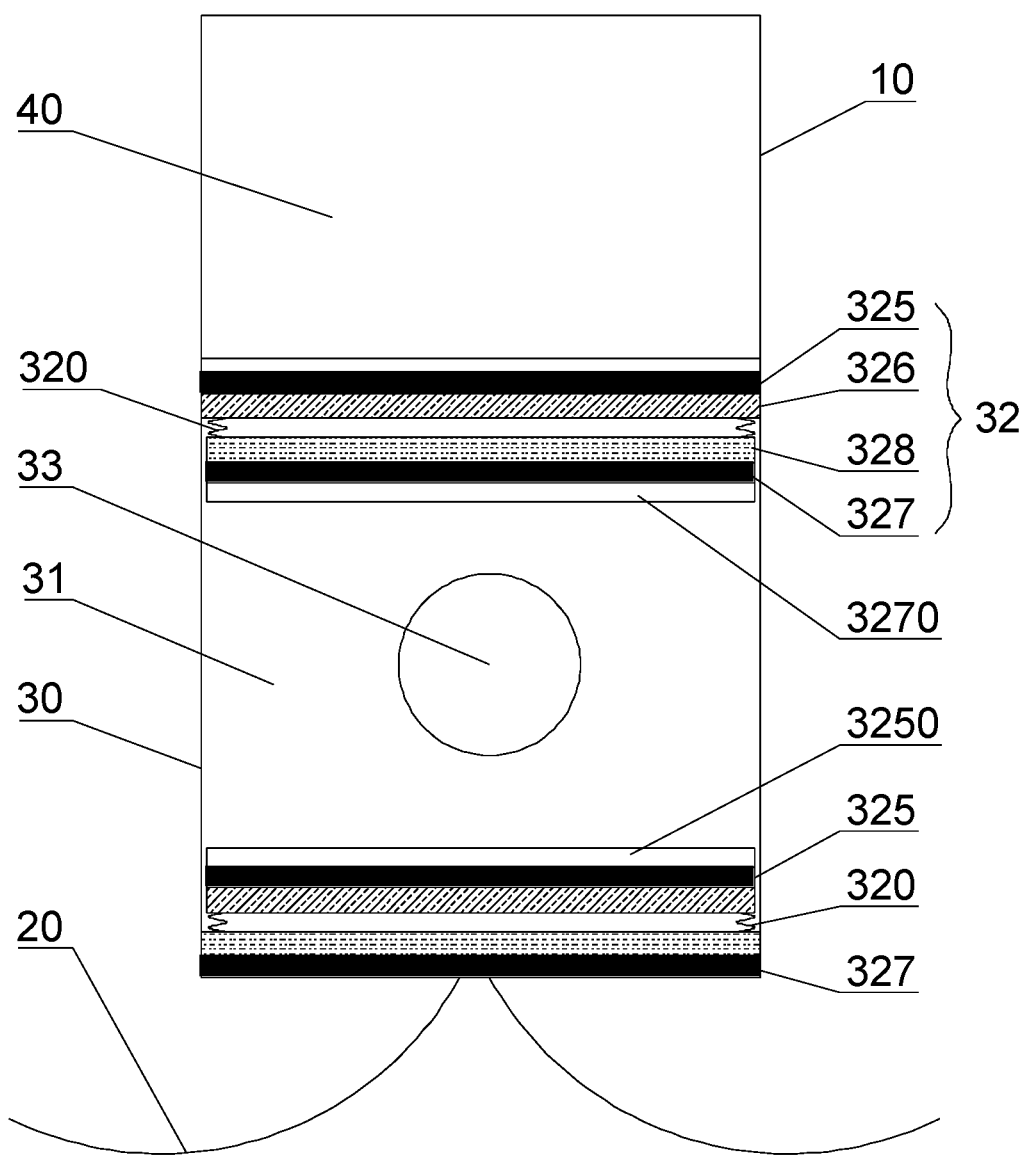
FIG. 9 is a schematic structural diagram of an intracardiac energy harvesting device according to some embodiments.
Figure 10:
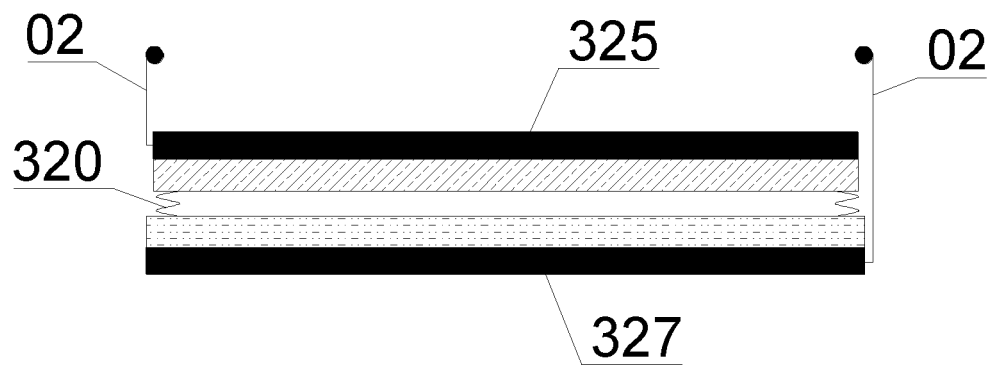
FIG. 10 is a schematic structural diagram of the power generation unit in FIG. 9.
Figure 11:
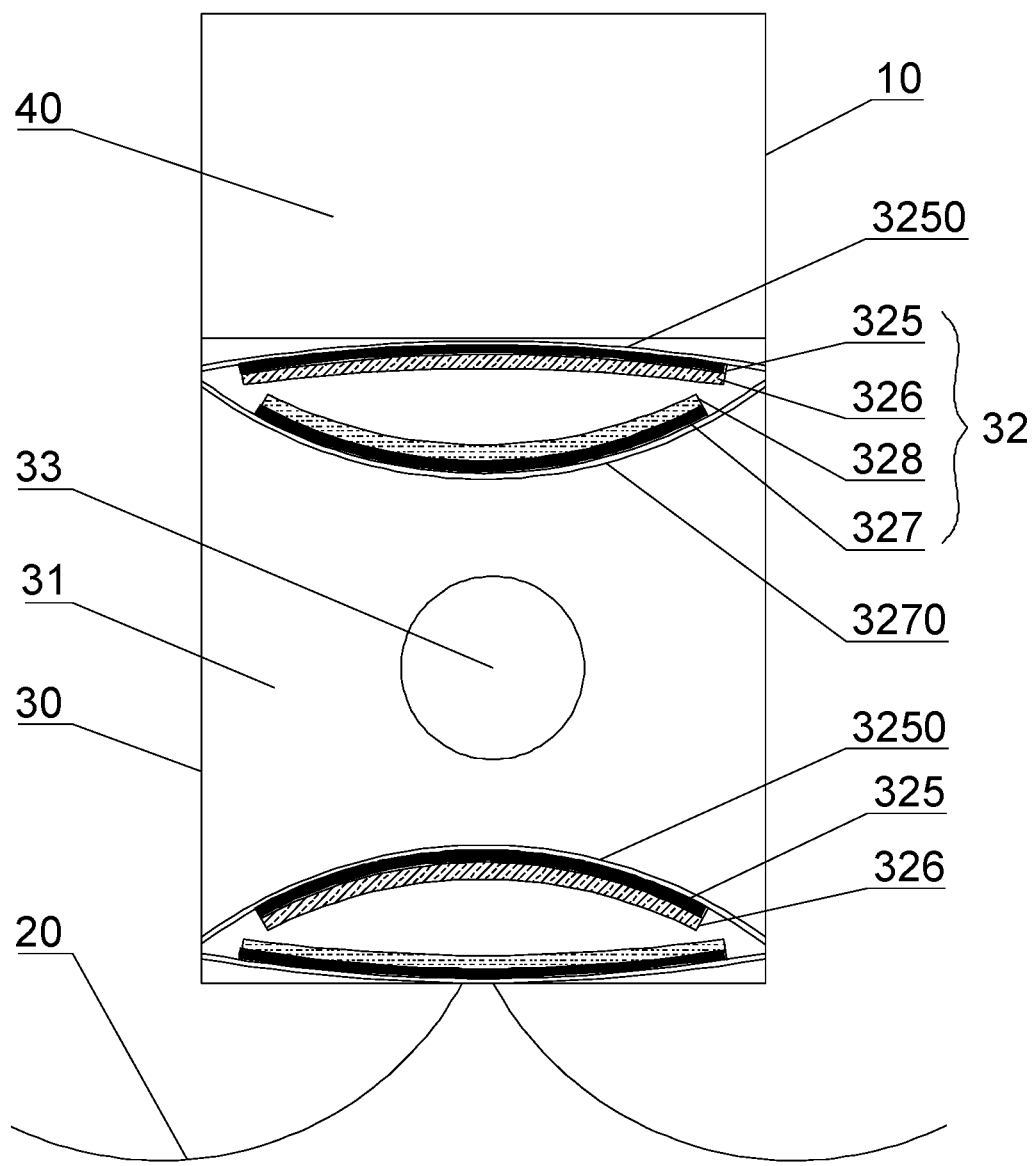
FIG. 11 is a schematic structural diagram of an intracardiac energy harvesting device according to some embodiments.

FIG. 9 is a schematic structural diagram of an intracardiac energy harvesting device according to some embodiments. FIG. 11 is a schematic structural diagram of an intracardiac energy harvesting device according to some embodiments.

Embodiment 2 differs from Embodiment 1 in that:

Referring to FIGS. 9 and 11, the power generation unit 32 is a triboelectric nanogenerator unit, and the power generation unit 32 includes a third electrode layer 325, a third friction layer 326 in contact with the third electrode layer 325, a fourth electrode layer 327, and a fourth friction layer 328 disposed in contact with the fourth electrode layer 327.

The third friction layer 326 and the fourth friction layer 328 are arranged face to face and are spaced apart from each other, and the first runout body 33 is configured to move in the first cavity 31 in response to the beating of the heart and apply a force to the third friction layer 326 and/or the fourth friction layer 328, so that the third friction layer 326 and the fourth friction layer 328 are in contact and separated, so that the third electrode layer 325 and the fourth electrode layer 327 output electrical signals to the power management module 40. The third electrode layer 325 and the fourth electrode layer 327 may be electrically connected to the input electrodes of the rectifying unit of the power management module 40 through the second wire 02, respectively. The third friction layer 326 and the fourth friction layer 328 are arranged face to face, and refer to both the third friction layer 326 and the fourth friction layer 328 being located between the third electrode layer 325 and the fourth electrode layer 327.

There is a difference in electronic capacity between the material of the third friction layer 326 and the material of the fourth friction layer 328, so that the contact surfaces of the third friction layer 326 and the fourth friction layer 328 contact or rub, so that contact charges can be generated on the contact surfaces of the third friction layer 326 and the fourth friction layer 328, one of the contact surfaces is positively charged, and the other contact surface is negatively charged. Each of the third friction layer 326 and the fourth friction layer 328 is selected from a group consisting of an insulator material, a semiconductor material, and a conductor material. The conventional insulating material has triboelectric characteristics and can be used as a material for preparing the third friction layer 326 and the fourth friction layer 328. Relative to the insulator, both the semiconductor and the metal have frictional electrical properties that tend to lose electrons, and thus, the semiconductor and metal can also be used as a material for the preparation of the third and fourth friction layers 326, 328. In this embodiment, each of the third friction layer 326 and the fourth friction layer 328 is selected from a group consisting of polyethylene, polypropylene, polystyrene, silica gel, polydimethylsiloxane, polyester, polyurethane, polymethacrylate, polytetrafluoroethylene and nylon, polyimide, nitrile rubber, fluororubber, latex, chitin, cellulose, gold, silver, copper, aluminum, iron and an alloy material, but is not limited thereto.

Each of the materials of the third electrode layer 325 and the material of the fourth electrode layer 327 is selected from a group consisting of a metal and a conductive polymer material, wherein the metal is selected from a group consisting of gold, silver, copper, aluminum, iron and an alloy, but is not limited thereto, and the conductive polymer material is selected from a group consisting of carbon nanotubes, graphene and carbon black, but is not limited thereto.

The third friction layer 326 or the fourth friction layer 328 may be prepared by replacing an insulating material or a semiconductor material with a conductor material, that is, the third friction layer 326 may be a conductor material, and instead of the third electrode layer 325 disposed in contact therewith, the fourth friction layer 328 may be a conductor material, and instead of the fourth electrode layer 327 disposed in contact therewith, the structure of the power generation unit 32 can be simplified, and the manufacturing cost is reduced. The conductor material may be selected from at least one of a metal, a conductive oxide, and a conductive polymer material.

At least one of the contact surfaces of the third friction layer 326 and the contact surface of the fourth friction layer 328 is selected from a group consisting of a micro-nano structure, a dot conjugate of the nanomaterial, and a coating of the nanomaterial. The micro-nano structure comprises micro-structures on the order of micron or submicron. The micro-structure is selected from a group consisting of nanowires, nanotubes, nanoparticles, nano-trenches, micro-trenches, nano-cones, micrometer cones, nanospheres, and micro-spherical structures, but is not limited thereto. A contact surface of the third friction layer 326 faces a surface of the fourth friction layer 328, and a contact surface of the fourth friction layer 328 faces a surface of the third friction layer 326. By adopting the arrangement, the contact area between the contact surface of the third friction layer 326 and the contact surface of the fourth friction layer 328 can be increased, so that the contact charge amount is increased, and the electrical signal output of the third electrode layer 325 and the fourth electrode layer 327 is facilitated.

A surface of the third electrode layer 325 away from the third friction layer 326 may be provided with a third substrate 3250, and/or a surface of the fourth electrode layer 327 away from the fourth friction layer 328 may be provided with a fourth substrate 3270, and when the first runout body 33 moves in the first cavity 31, contact and separation between the third friction layer 326 and the fourth friction layer 328 are caused by impacting the third substrate 3250 and/or the fourth substrate 3270, so that the third electrode layer 325 and the fourth electrode layer 327 output electrical signals to the power management module 40.

The third electrode layer 325 may be directly fixed on the inner wall of the first cavity 31 or fixed to the inner wall of the first cavity 31 through the third substrate 3250. The inner wall of the first cavity 31 is selected from a group consisting of a top wall, a bottom wall and a side wall of the first cavity 31. At this time, when the first runout body 33 moves in the first cavity 31, the third friction layer 326 and the fourth friction layer 328 are in contact and separated by impacting the fourth substrate 3270. Between the inner wall of the first cavity 31 and the fourth substrate 3270, between the inner wall of the first cavity 31 and the fourth substrate 3270, between the third substrate 3250 and the fourth substrate 3270, at least one of the third substrate 3250 and the fourth substrate 3270, between the third substrate 3250 and the fourth substrate 3270, at least one of the third friction layer 326 and the fourth friction layer 328 may be provided with at least one support member 320, and the third friction layer 326 and the fourth friction layer 328 are supported by the support member 320 so that the third friction layer 326 and the fourth friction layer 328 are spaced apart from each other by a certain space. The support 320 may be an elastic support or a non-elastic support. When the supporting piece 320 is an elastic supporting piece, the supporting piece 320 can be a spring. However, the support 320 is not limited thereto and may include various other resilient members. When the first runout body 33 moves in the first cavity 31, the support member 320 is subjected to force compression by impacting the fourth substrate 3270, thereby making contact and separation between the third friction layer 326 and the fourth friction layer 328. At least one of the third substrate 3250 and the fourth substrate 3270 may have a flexible material that is flexible to return to its initial state as the impact force of the first runout body 33 is removed, or at least one of the third substrate 3250 and the fourth substrate 3270 may include a material having flexibility to deform to extend or contract due to external forces. For example, at least one of the third substrate 3250 and the fourth substrate 3270 may include polyester (PE), polyethersulfone (PES), polyethylene naphthalate (PEN), or polyimide (PI), but is not limited thereto. The third electrode layer 325 and the third friction layer 326 may have flexibility and stretchability corresponding to the third substrate 3250, and the fourth electrode layer 327 and the fourth friction layer 328 may have flexibility and stretchability corresponding to the fourth substrate 3270.

The fourth electrode layer 327 may be directly fixed on the inner wall of the first cavity 31 or fixed to the inner wall of the first cavity 31 through the fourth substrate 3270. The inner wall of the first cavity 31 is selected from a group consisting of a top wall, a bottom wall and a side wall of the first cavity 31. At this time, when the first runout body 33 moves in the first cavity 31, that is, the third substrate 3250 is impacted, so that the third friction layer 326 and the fourth friction layer 328 are in contact and separated. Between the inner wall of the first cavity 31 and the third substrate 3250, between the inner wall of the first cavity 31 and the third substrate 3250, between the fourth substrate 3270 and the third substrate 3250, at least one of the fourth substrate 3270 and the third substrate 3250, at least one of the fourth friction layer 328 and the third substrate 3250, the fourth friction layer 328 and the third friction layer 326 may be provided with at least one support member 320, and the third friction layer 326 and the fourth friction layer 328 are spaced apart from each other by means of the support member 320. When the first runout body 33 moves in the first cavity 31, the support member 320 is subjected to force compression by impacting the third substrate 3250, thereby making contact and separation between the third friction layer 326 and the fourth friction layer 328. At least one of the third substrate 3250 and the fourth substrate 3270 may have a flexible material that is flexible to return to its initial state as the impact force of the first runout body 33 is removed, or at least one of the third substrate 3250 and the fourth substrate 3270 may include a material having flexibility to deform to extend or contract due to external forces.

Figure 12:
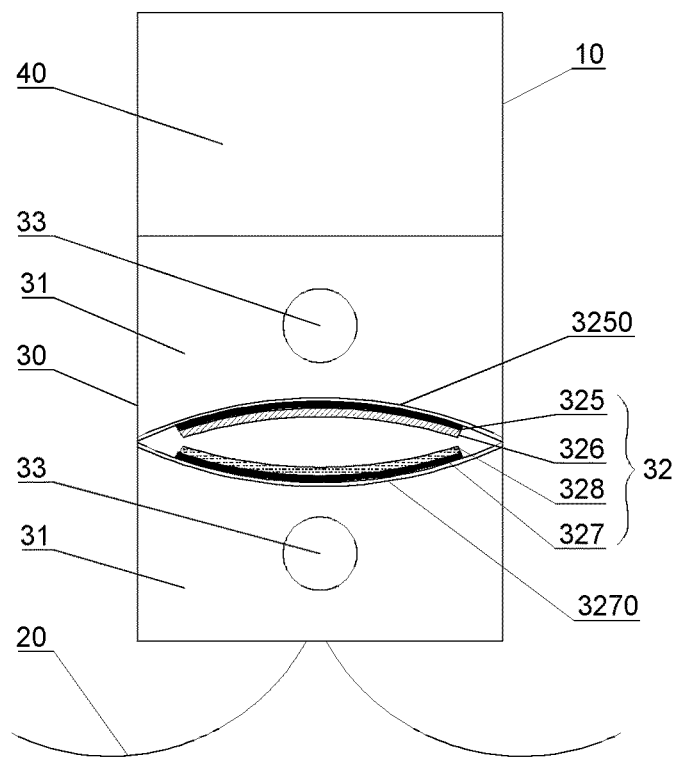
FIG. 12 is a schematic structural diagram of an intracardiac energy harvesting device modified from FIG. 11.

FIG. 12 is a schematic structural diagram of an intracardiac energy harvesting device modified from FIG. 11.

Referring to FIG. 12, the outer edge of the third substrate 3250 and the outer edge of the fourth substrate 3270 may be both fixed on the side wall of the first cavity 31, so that space is formed on both sides of the power generation unit 32, the first runout body 33 located on one side of the third substrate 3250 impacts the third substrate 3250 during movement, and the first runout body 33 located on one side of the fourth substrate 3270 impacts the fourth substrate 3270 during movement, thereby making contact and separation between the third friction layer 326 and the fourth friction layer 328. At this point, each of the third substrate 3250 and the fourth substrate 3270 may include a material that is flexible to return to its initial state as the impact force of the first runout body 33 is removed, or each of the third and fourth substrates 3250, 3270 may include a material having flexibility to deform to extend or contract due to impact forces of the first runout body 33. The third electrode layer 325 and the third friction layer 326 may have flexibility and stretchability corresponding to the third substrate 3250, and the fourth electrode layer 327 and the fourth friction layer 328 may have flexibility and stretchability corresponding to the fourth substrate 3270. When the third substrate 3250 and the fourth substrate 3270 are in a natural state, the third substrate 3250 and the fourth substrate 3270 may be arc-shaped or arched.

Referring to FIG. 9 and FIG. 11, the number of the power generation units 32 is multiple, the two adjacent power generation units 32 are spaced apart by a space for free movement of the at least one first runout body 33, and when the shell 10 moves along with the heart beat, the third substrate 3250 and/or the fourth substrate 3270 of each power generation unit 32 are impacted by the first runout body 33, so that the third electrode layer 325 and the fourth electrode layer 327 of each power generation unit 32 output electrical signals to the rectifier unit of the power management module 40.

The power management module 40 may include at least one rectification unit corresponding to the number of power generation units 32, each power generation unit 32 is connected to a rectifying unit, and the output ends of all the rectifying units are connected in parallel. By adopting the arrangement, the overall current output of the nanogenerator module 30 can be improved.

Figure 13:
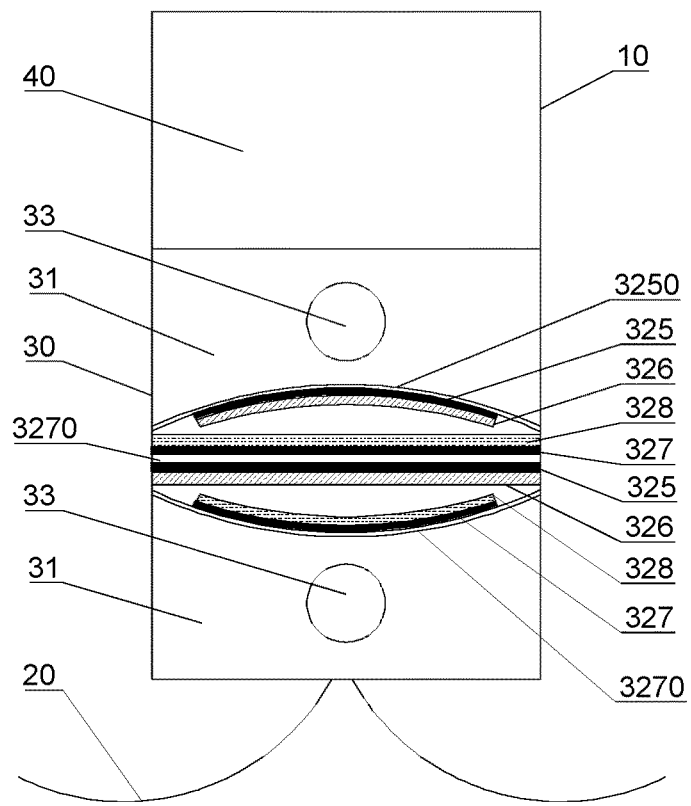
FIG. 13 is a schematic structural diagram of an intracardiac energy harvesting device modified from FIG. 11.

FIG. 13 is a schematic structural diagram of an intracardiac energy harvesting device modified from FIG. 11.

Referring to FIG. 13, the plurality of power generation units 32 may be stacked, and the two adjacent power generation units 32 may be separated from each other by means of a third substrate 3250 and/or a fourth substrate 3270, so that each power generation unit 32 is separately connected to a rectification unit, and the output ends of all the rectification units are connected in parallel.

Figure 14:
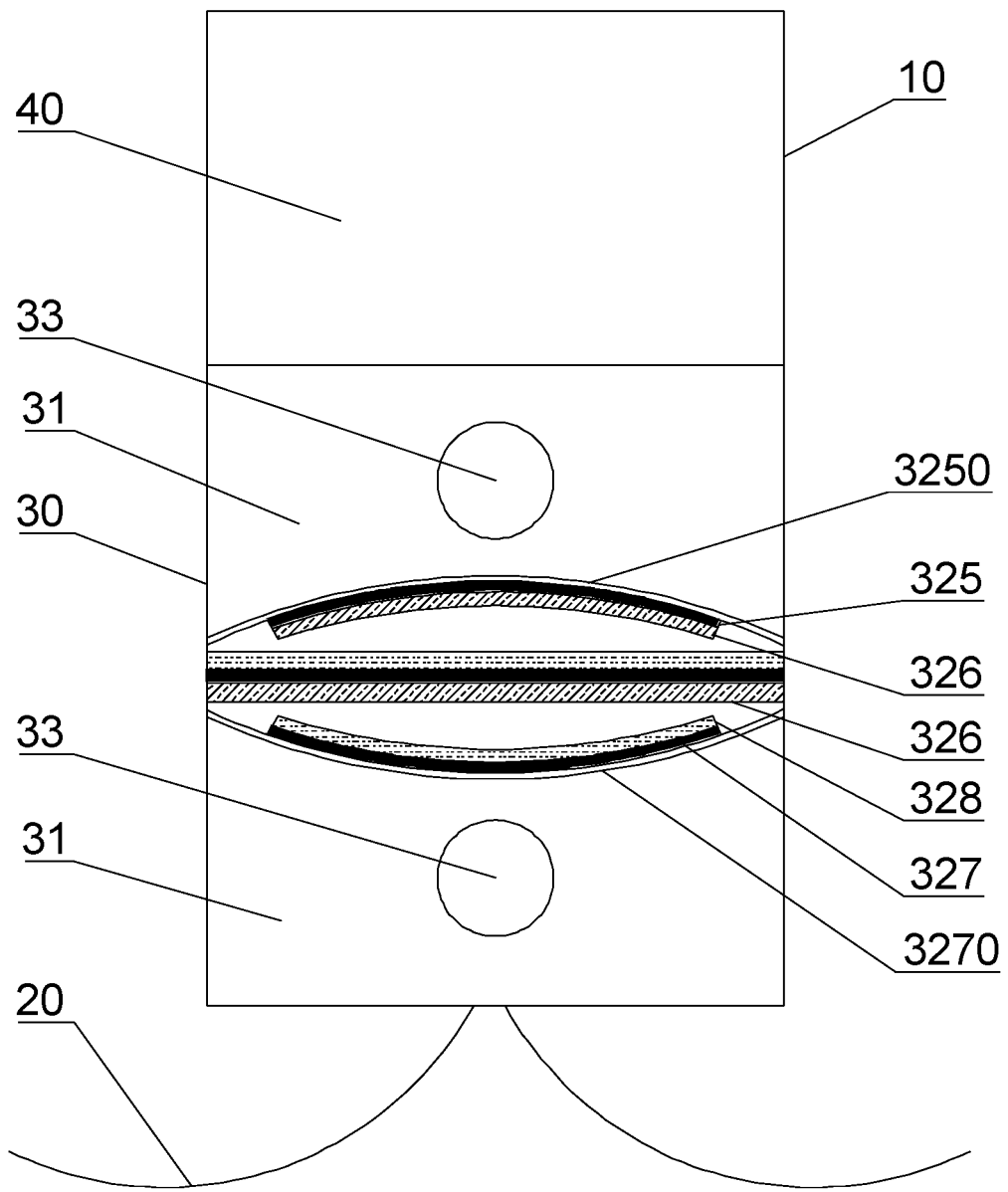
FIG. 14 is a schematic structural diagram of an intracardiac energy harvesting device modified from FIG. 11.

FIG. 14 is a schematic structural diagram of an intracardiac energy harvesting device modified from FIG. 11.

Referring to FIG. 14, it should be noted that the third substrate 3250 and/or the fourth substrate 3270 may not be disposed between two adjacent power generation units 32, and the same electrode layer may be shared between two adjacent power generation units 32.

Embodiment 3

The present embodiment provides an intracardiac energy harvesting device 100 having a size and shape adapted to be implanted into the interior of a heart chamber by an interventional procedure. The intracardiac energy harvesting device 100 comprises a shell 10, a fixing mechanism 20, a nanogenerator module 30, and a power management module 40.

The nanogenerator module 30 comprises a first cavity 31, at least one power generation unit 32 and at least one first runout body 33.

The first cavity 31 is a cavity inside the shell 10.

The at least one power generation unit 32 is disposed in the first cavity 31, and the power generation unit 32 may be disposed on at least one of the top wall, the bottom wall and the side wall of the first cavity 31. The at least one power generation unit 32 is selected from a group consisting of a triboelectric nanogenerator unit and a triboelectric nanogenerator.

At least one of the first runout bodies 33 is freely movably disposed in the first cavity 31, that is, when the heart beats and drives the shell 10 to move through the fixing mechanism 20, the shell 10 drives the first runout body 33 to move in the first cavity 31. The first runout body 33 is configured to move in the first cavity 31 and make contact with and/or impact the power generation unit 32 in response to the beating of the heart (i.e., contraction and contraction of the heart), so that the power generation unit 32 outputs an electrical signal to the power management module 40. The first runout body 33 can be integrally formed, and can also be a multi-layer combined runout body.

In embodiment 1, the power generation unit 32 includes a first electrode layer 321, a first friction layer 322 disposed in contact with the first electrode layer 321, a second electrode layer 323, and a second friction layer 324 disposed in contact with the second electrode layer 323.

Figure 15:
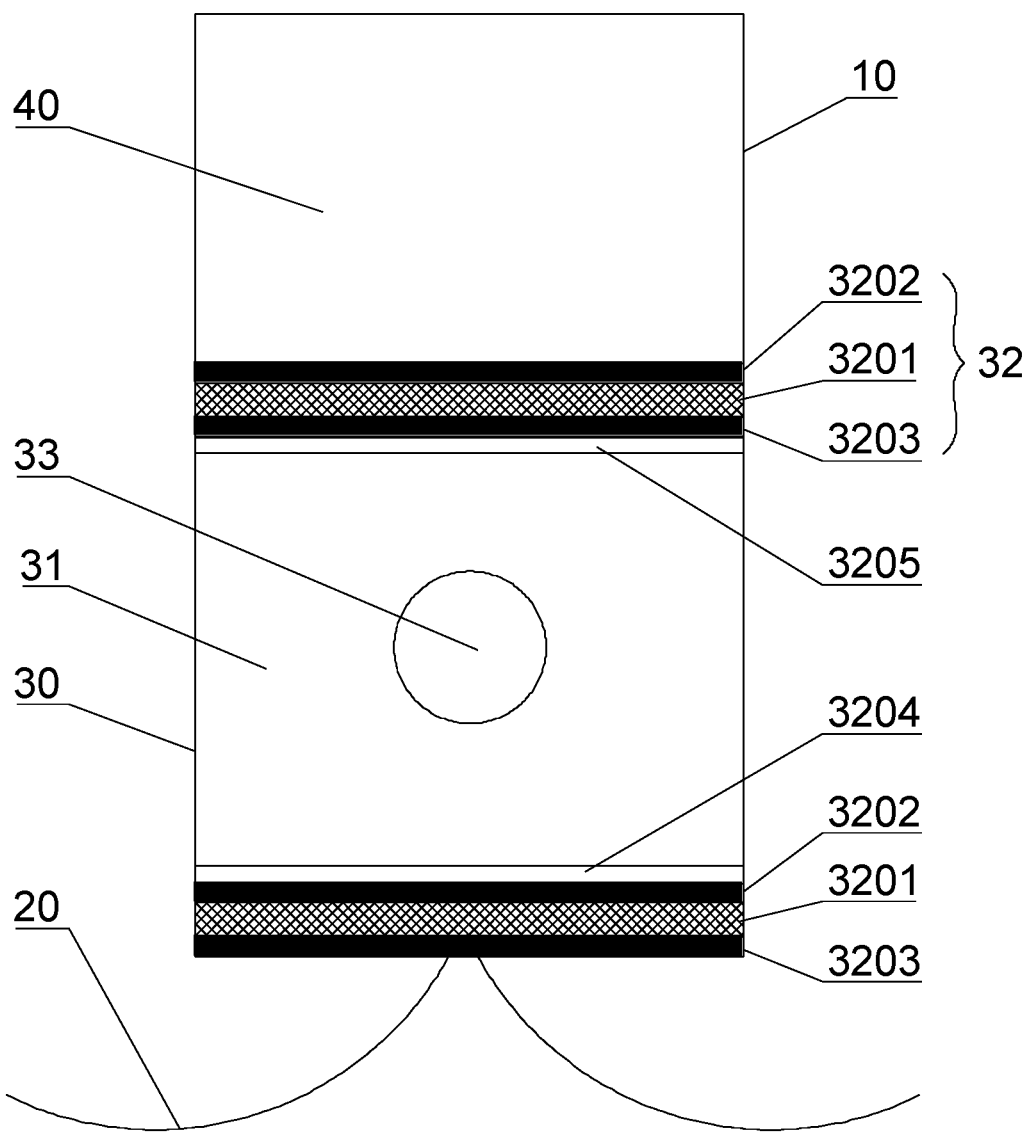
FIG. 15 is a schematic structural diagram of an intracardiac energy harvesting device according to some embodiments.

FIG. 15 is a schematic structural diagram of an intracardiac energy harvesting device according to some embodiments.

Embodiment 3 differs from Embodiment 1 in that:

Referring to FIG. 15, the power generation unit 32 is a triboelectric nanogenerator, the power generation unit 32 comprises a piezoelectric material layer 3201, a first piezoelectric electrode layer 3202 disposed in contact with the piezoelectric material layer 3201 and located on one side of the piezoelectric material layer 3201, and a second piezoelectric electrode layer 3203 disposed in contact with the piezoelectric material layer 3201 and located on the other side of the piezoelectric material layer 3201.

The first runout body 33 is configured to move in the first cavity 31 in response to the beating of the heart and apply a force to the piezoelectric material layer 3201, so that the first piezoelectric electrode layer 3202 and the second piezoelectric electrode layer 3203 output electrical signals to the power management module 40. The first piezoelectric electrode layer 3202 and the second piezoelectric electrode layer 3203 may be electrically connected to an input electrode of a rectifying unit of the power management module 40 through a third wire, respectively.

Each of the first piezoelectric electrode layer 3202 and the second piezoelectric electrode layer 3203 is selected from a group consisting of a metal conductor material, a metal alloy conductor material, a metal oxide conductor material (e.g., indium oxide), but is not limited thereto.

The piezoelectric material layer 3201 is selected from a group consisting of a piezoelectric ceramic, an oxide, and a polymer, for example, the piezoelectric material layer 3201 is selected from a group consisting of lead zirconate titanate (PZT), zinc oxide and polyvinylidene fluoride (PVDF), but is not limited thereto. The piezoelectric polarization direction of the triboelectric nanogenerator can be up and down, which is not limited herein.

A surface of the first piezoelectric electrode layer 3202 away from the piezoelectric material layer 3201 may be provided with a first substrate 3204, and a surface of the second piezoelectric electrode layer 3203 away from the piezoelectric material layer 3201 may be provided with a second substrate 3205.

The first piezoelectric electrode layer 3202 can be directly fixed on the inner wall of the first cavity 31 or fixed to the inner wall of the first cavity 31 through the first substrate 3204. When the first bouncing body 33 moves in the first cavity 31, the piezoelectric material layer 3201 is stressed to deform by impacting the second substrate 3205, so that a potential difference is generated on the upper surface and the lower surface of the piezoelectric material layer 3201, opposite charges are induced on the surface of the first piezoelectric electrode layer 3202 and the second piezoelectric electrode layer 3203, and the electric energy is output to the rectifier unit of the power management module 40 under the condition that the external circuit is switched on.

The second piezoelectric electrode layer 3203 may be directly fixed on the inner wall of the first cavity 31 or fixed to the inner wall of the first cavity 31 by means of the second substrate 3205. When the first bouncing body 33 moves in the first cavity 31, the piezoelectric material layer 3201 is stressed to deform by impacting the first substrate 3204, so that a potential difference is generated on the upper surface and the lower surface of the piezoelectric material layer 3201, opposite charges are induced on the surface of the first piezoelectric electrode layer 3202 and the second piezoelectric electrode layer 3203, and the electric energy is output to the rectifying unit of the power management module 40 under the condition that the external circuit is switched on.

Figure 16:
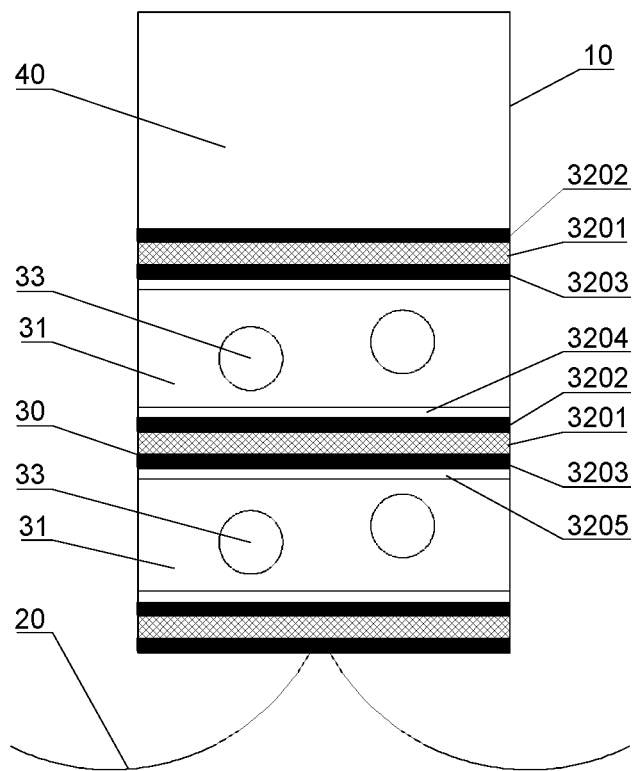
FIG. 16 is a schematic structural diagram of an intracardiac energy harvesting device modified from FIG. 15.

FIG. 16 is a schematic structural diagram of an intracardiac energy harvesting device modified from FIG. 15.

Referring to FIG. 16, the outer edge of the first substrate 3204 and the outer edge of the second substrate 3205 may be both fixed on the side wall of the first cavity 31, so that the two sides of the power generation unit 32 both form a space, the first runout body 33 located on one side of the first substrate 3204 impacts the first substrate 3204, and the first runout body 33 located on one side of the second substrate 3205 impacts the second substrate 3205 when moving, so that the first piezoelectric electrode layer 3202 and the second piezoelectric electrode layer 3203 output electrical energy to the rectifier unit of the power management module 40.

Each of the first substrate 3204 and the second substrate 3205 may be a flexible material or a non-flexible material. At least one of the first substrate 3204 and the second substrate 3205 may include a material having flexibility to deform to extend or contract due to impact forces of the first runout body 33.

It should be noted that the structure of the triboelectric nanogenerator is merely an example, and in practice, the specific structure of the triboelectric nanogenerator is not limited in this embodiment, that is, the triboelectric nanogenerator of any structure can be applied to the structure of the intracardiac energy harvesting device 100 according to the present embodiment.

As shown in FIG. 15 and FIG. 16, the number of the power generation units 32 is multiple, the adjacent two power generation units 32 are spaced apart by a space allowing the at least one first runout body 33 to move freely, and when the shell 10 moves along with the heart beat, the first runout body 33 impacts the first substrate 3204 and/or the second substrate 3205 of each power generation unit 32, so that the piezoelectric material layer 3201 of each power generation unit 32 is stressed to deform, and the first piezoelectric electrode layer 3202 and the second piezoelectric electrode layer 3203 of each power generation unit 32 output electrical energy to the rectifier unit of the power management module 40.

The power management module 40 may include at least one rectification unit corresponding to the number of power generation units 32, each power generation unit 32 is connected to a rectifying unit, and the output ends of all the rectifying units are connected in parallel. By adopting the arrangement, the overall current output of the nanogenerator module 30 can be improved.

Figure 17:
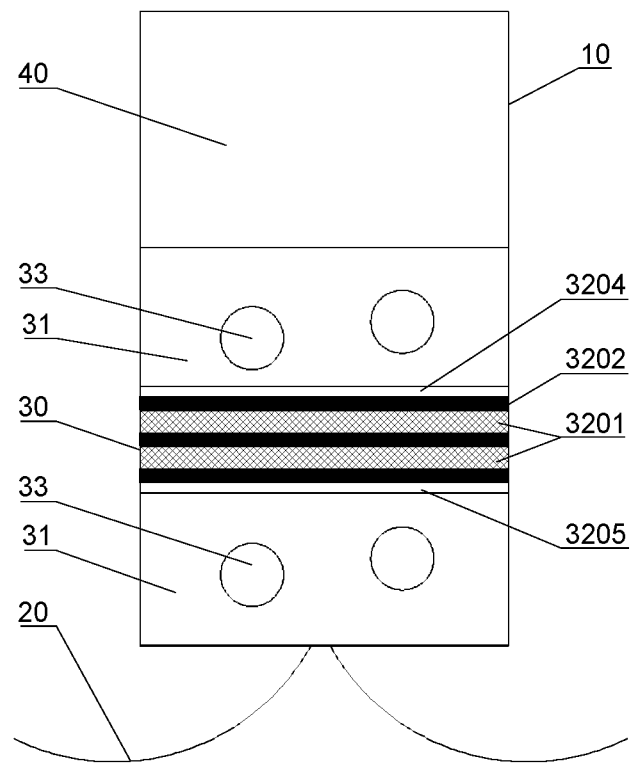
FIG. 17 is a schematic structural diagram of an intracardiac energy harvesting device modified from FIG. 15.

The plurality of power generation units 32 may be stacked, and the two adjacent power generation units 32 may be separated from each other by means of the first substrate 3204 and/or the second substrate 3205, so that each power generation unit 32 is separately connected to a rectifying unit, and the output ends of all the rectifying units are connected in parallel. It should be noted that the first substrate 3204 and/or the second substrate 3205 may not be disposed between two adjacent power generation units 32, and the same piezoelectric electrode layer may be shared. FIG. 17 shows an example of sharing the same piezoelectric electrode layer between two adjacent power generation units 32.

Embodiment 4

The present embodiment provides an intracardiac energy harvesting device 100 having a size and shape adapted to be implanted into the interior of a heart chamber by an interventional procedure. The intracardiac energy harvesting device 100 comprises a shell 10, a fixing mechanism 20, a nanogenerator module 30, and a power management module 40.

The nanogenerator module 30 comprises a first cavity 31, at least one power generation unit 32 and at least one first runout body 33.

The first cavity 31 is a cavity inside the shell 10.

The at least one power generation unit 32 is disposed in the first cavity 31, and the power generation unit 32 may be disposed on at least one of the top wall, the bottom wall and the side wall of the first cavity 31. The at least one power generation unit 32 is selected from a group consisting of a triboelectric nanogenerator unit and a triboelectric nanogenerator.

At least one of the first runout bodies 33 is freely movably disposed in the first cavity 31, that is, when the heart beats and drives the shell 10 to move through the fixing mechanism 20, the shell 10 drives the first runout body 33 to move in the first cavity 31. The first runout body 33 is configured to move in the first cavity 31 and make contact with and/or impact the power generation unit 32 in response to the beating of the heart (i.e., contraction and contraction of the heart), so that the power generation unit 32 outputs an electrical signal to the power management module 40. The first runout body 33 can be integrally formed, and can also be a multi-layer combined runout body.

In embodiment 1, the power generation unit 32 includes a first electrode layer 321, a first friction layer 322 disposed in contact with the first electrode layer 321, a second electrode layer 323, and a second friction layer 324 disposed in contact with the second electrode layer 323.

Figure 18:
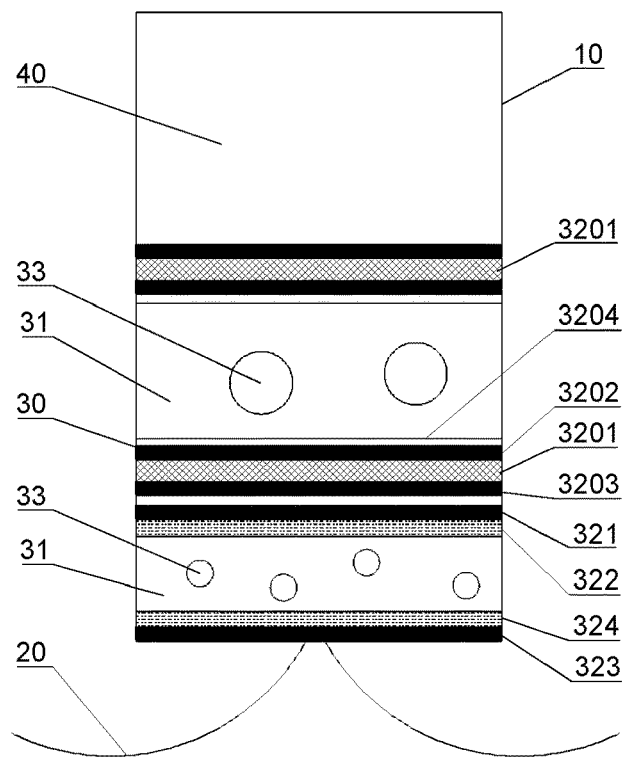
FIG. 18 is a schematic structural diagram of an intracardiac energy harvesting device according to some embodiments.
Figure 19:
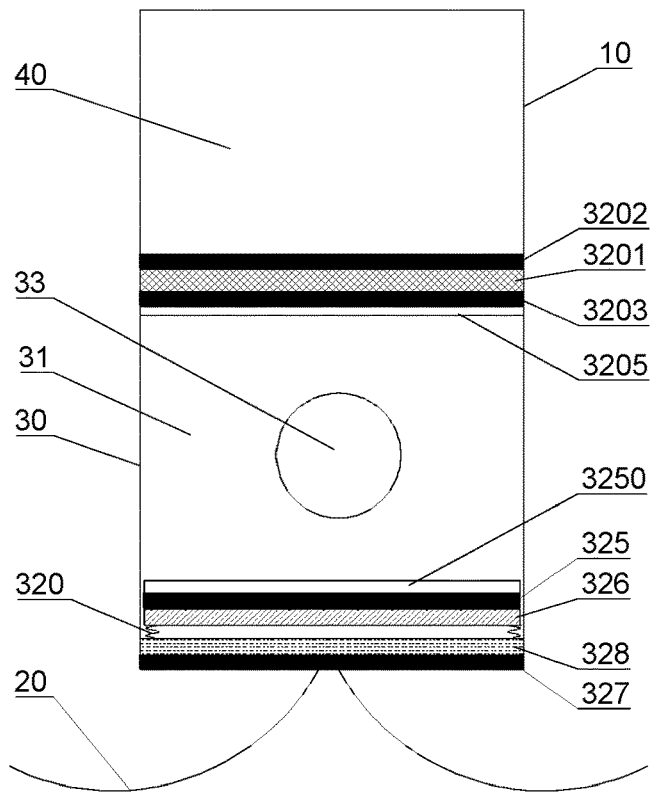
FIG. 19 is a schematic structural diagram of an intracardiac energy harvesting device according to some embodiments.
Figure 20:
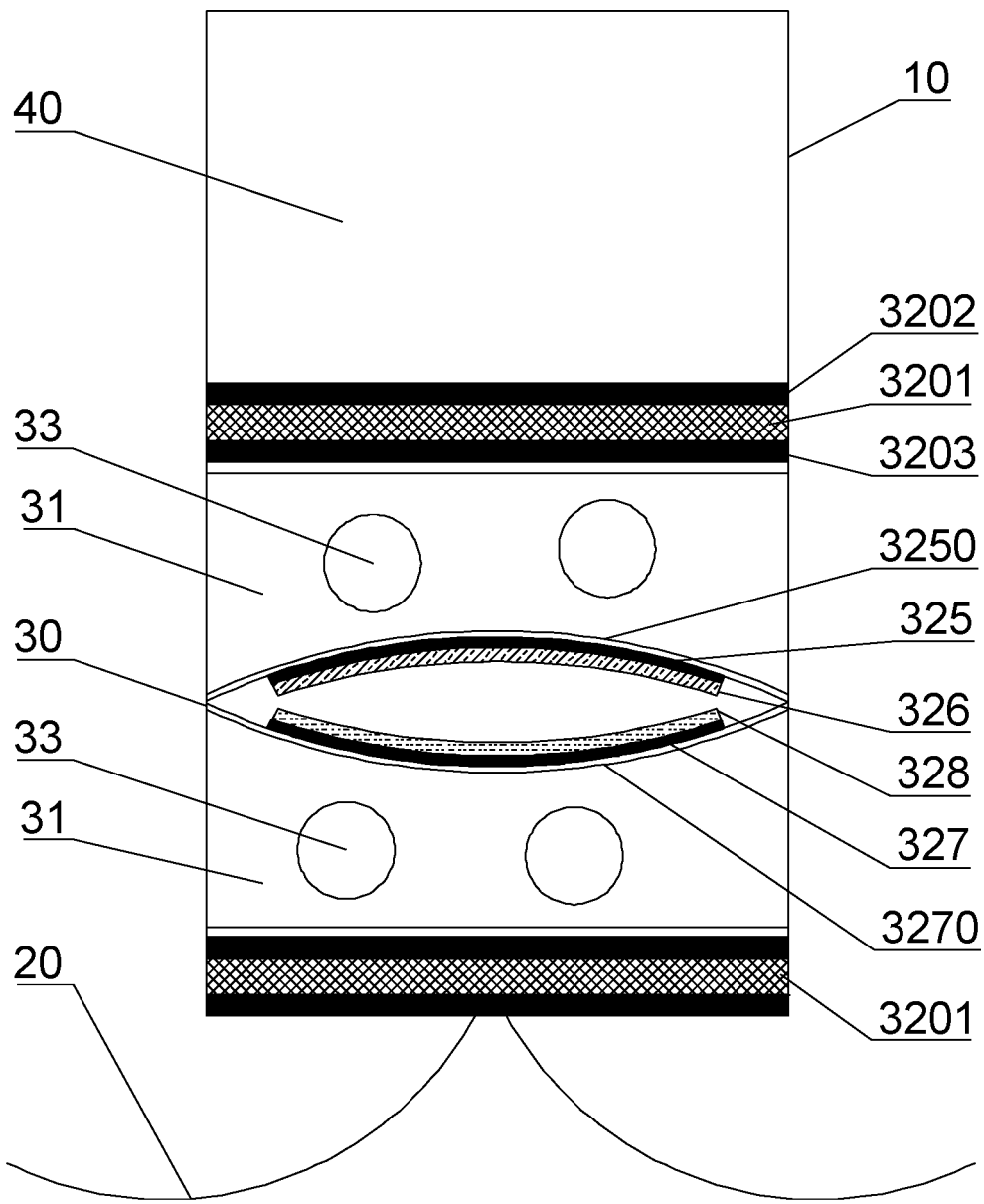
FIG. 20 is a schematic structural diagram of an intracardiac energy harvesting device according to some embodiments.

FIGS. 18-20 is a schematic structural diagram of an intracardiac energy harvesting device according to some embodiments.

Embodiment 4 differs from Embodiment 1 in that:

Referring to FIGS. 18-20, at least two power generation units 32 are arranged in the first cavity 31, and the at least two power generation units 32 comprise at least one triboelectric nanogenerator unit and at least one triboelectric nanogenerator.

The first runout body 33 is configured to contact and/or impact the triboelectric nanogenerator unit and/or the triboelectric nanogenerator in response to the beating of the heart, so that the triboelectric nanogenerator unit and/or the triboelectric nanogenerator output an electrical signal to the power management module 40, respectively.

The at least one triboelectric nanogenerator unit is selected from a group consisting of the triboelectric nanogenerator unit in Embodiment 1 and the triboelectric nanogenerator unit in Embodiment 2. FIG. 18 shows an example of a triboelectric nanogenerator unit in Embodiment 1. FIG. 19 and FIG. 20 illustrate an example of using the triboelectric nanogenerator unit in Embodiment 2. The at least one triboelectric nanogenerator can be the triboelectric nanogenerator in Embodiment 3.

At least one triboelectric nanogenerator unit and at least one triboelectric nanogenerator can be spaced apart from each other by a space for free movement of at least one first runout body 33, and the triboelectric nanogenerator unit and the triboelectric nanogenerator are repeatedly contacted and/or hit by moving the first runout body 33 in the space, so that the triboelectric nanogenerator unit and the triboelectric nanogenerator output electrical signals to the power management module 40, respectively.

The at least one triboelectric nanogenerator unit and the at least one triboelectric nanogenerator can be stacked, and the adjacent triboelectric nanogenerator units and the triboelectric nanogenerator s can be separated through the substrate, so that each triboelectric nanogenerator unit and each triboelectric nanogenerator are separately connected with a rectification unit, and the output ends of all the rectification units are connected in parallel. FIG. 18 shows an example of an adjacent triboelectric nanogenerator unit and a triboelectric nanogenerator separated by a substrate. It should be noted that the adjacent triboelectric nanogenerator unit and the triboelectric nanogenerator can also not be provided with a substrate, and the adjacent triboelectric nanogenerator unit and the triboelectric nanogenerator can share the same electrode layer.

Embodiment 5

The present embodiment provides an intracardiac energy harvesting device 100 having a size and shape adapted to be implanted into the interior of a heart chamber by an interventional procedure. The intracardiac energy harvesting device 100 comprises a shell 10, a fixing mechanism 20, a nanogenerator module 30, and a power management module 40.

In Embodiment 1, the nanogenerator module 30 comprises a first cavity 31, at least one power generation unit 32, and at least one first runout body 33, wherein the first runout body 33 is configured to move in the first cavity 31 and contact and/or impact the power generation unit 32 in response to the beating of the heart, so that the power generation unit 32 outputs an electrical signal to the power management module 40.

Figure 21:
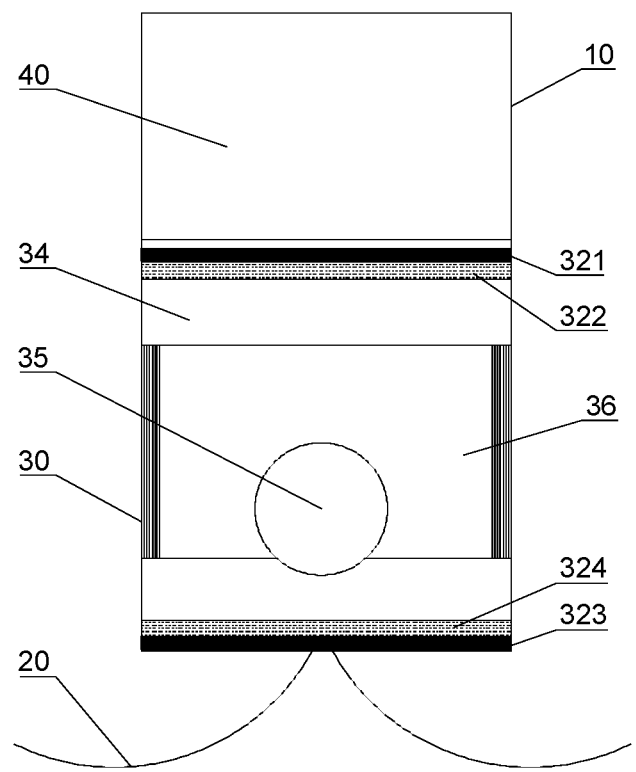
FIG. 21 is a schematic structural diagram of an intracardiac energy harvesting device according to some embodiments.
Figure 22:
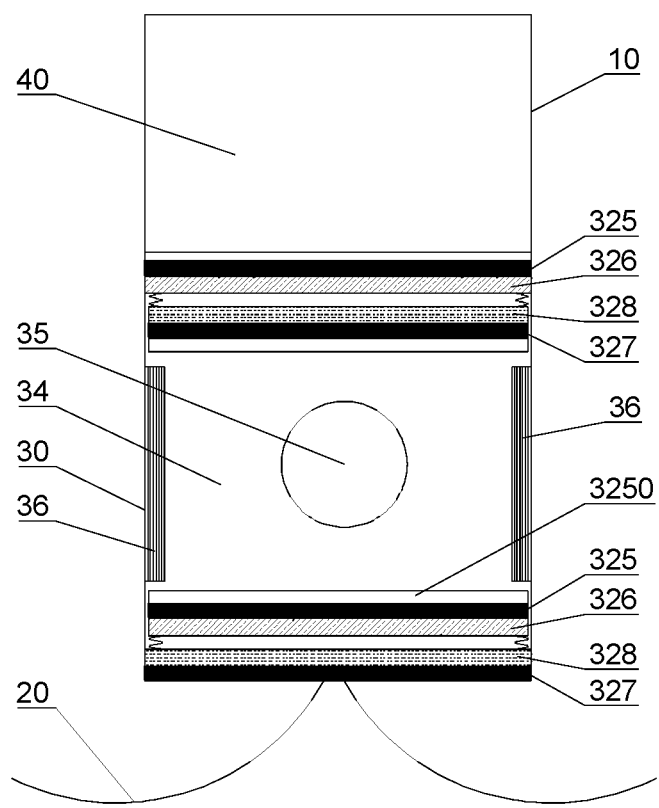
FIG. 22 is a schematic structural diagram of an intracardiac energy harvesting device according to some embodiments.
Figure 23:
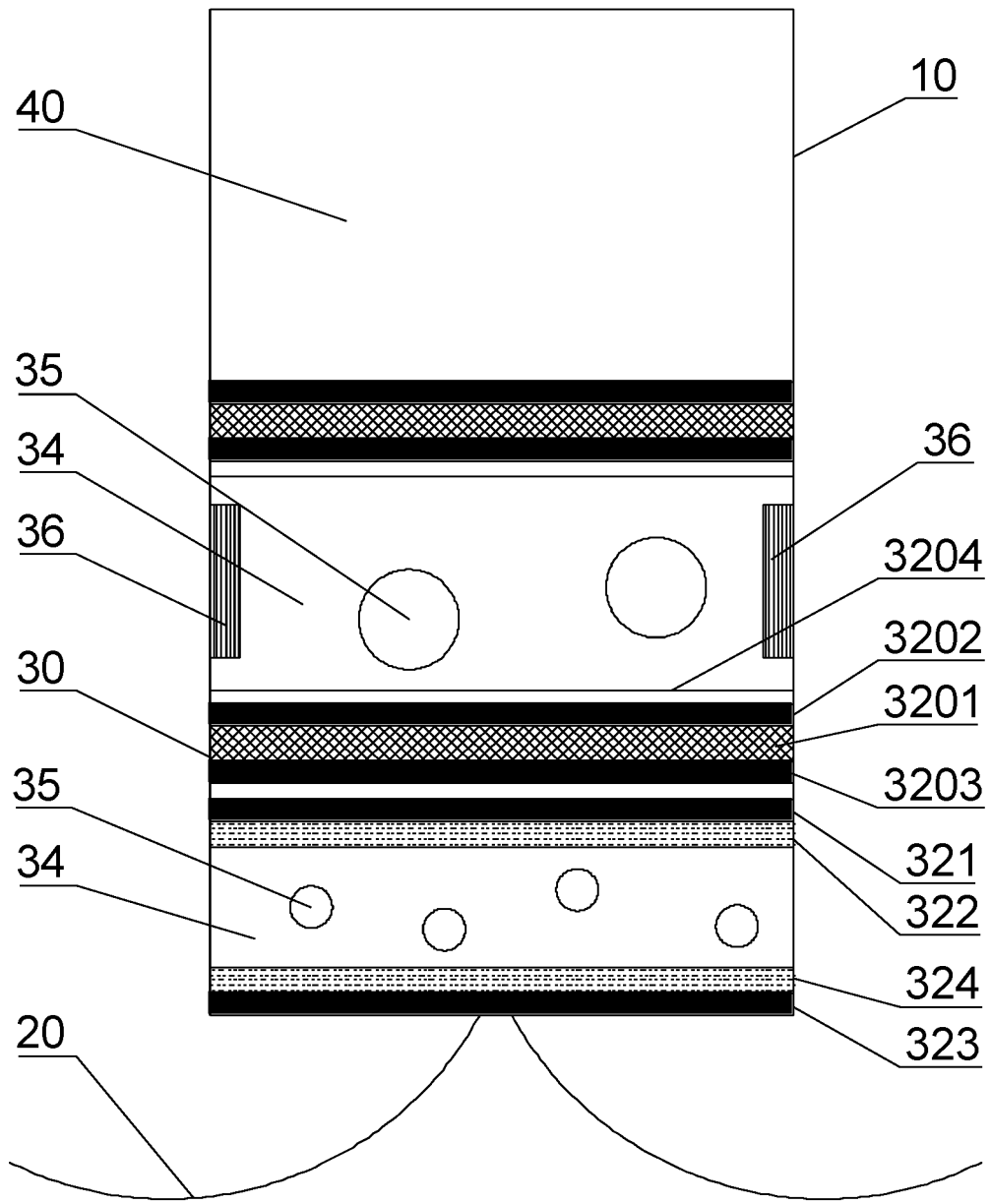
FIG. 23 is a schematic structural diagram of an intracardiac energy harvesting device according to some embodiments.

FIG. 21 to FIG. 23 are schematic structural diagrams of an intracardiac energy harvesting device according to some embodiments.

Embodiment 5 differs from Embodiment 1 in that:

Referring to FIGS. 21-23, the nanogenerator module 30 includes a second cavity 34, at least one triboelectric nanogenerator unit, and/or at least one triboelectric nanogenerator, at least one second runout body 35, and at least one coil 36.

The second cavity 34 is a cavity inside the shell 10.

The at least one triboelectric nanogenerator unit and/or the at least one triboelectric nanogenerator are both disposed in the second cavity 34, and the at least one triboelectric nanogenerator unit is selected from a group consisting of the triboelectric nanogenerator unit in Embodiment 1 and the triboelectric nanogenerator unit in Embodiment 2. FIG. 21 shows an example of a triboelectric nanogenerator unit in Embodiment 1. FIG. 22 shows an example of a triboelectric nanogenerator unit in Embodiment 2. The at least one triboelectric nanogenerator can be the triboelectric nanogenerator in Embodiment 3. FIG. 22 shows an example of a triboelectric nanogenerator in Embodiment 3.

At least one second runout body 35 is freely movably disposed in the second cavity 34, that is, when the heart beats and drives the shell 10 to move through the fixing mechanism 20, the shell 10 drives the second runout body 35 to move in the second cavity 34. Moreover, the second runout body 35 includes a magnet to cause the second runout body 35 to generate an alternating magnetic field during movement of the second cavity 34. The second runout body 35 may be a magnet as a whole. When at least one triboelectric nanogenerator unit comprises the triboelectric nanogenerator unit in Embodiment 1, the second runout body 35 may comprise a magnet and a friction material provided on the outer surface of the magnet, and the friction material may be a material of the first runout body 33 in Embodiment 1. The magnet is selected from a group consisting of neodymium iron boron, aluminum nickel cobalt, samarium cobalt and ferrite.

At least one coil 36 is fixed in the second cavity 34, at least one coil 36 can be fixed on the inner wall of the second cavity 34, and the inner wall of the second cavity 34 is selected from a group consisting of a top wall, a bottom wall and a side wall of the first cavity 31. The coil 36 is used for relatively cutting the magnetic induction lines in the alternating magnetic field generated by the movement of the second runout body 35 in the second cavity 34, so that alternating current is generated in the coil 36, and a magnetoelectric potential difference is formed. Two ends of the coil 36 may be electrically connected to an input electrode of the rectifying unit of the power management module 40 through a fourth wire, respectively. The coil 36 may be a planar coil, and the coil 36 may be a single-phase or concentric-winding annular coil.

The second runout body 35 is configured to move in the second cavity 34 in response to the runout of the heart to make contact and/or impact the triboelectric nanogenerator 32 and/or the triboelectric nanogenerator 32 and generate an alternating magnetic field, so that the triboelectric nanogenerator 32 and/or the triboelectric nanogenerator 32 outputs an electrical signal to the power management module 40, and outputs a magnetic electrical signal to the power management module 40 relative to the magnetic induction line in the alternating magnetic field.

By means of the arrangement, the shell 10 moves along with the beating of the heart, thereby driving the second runout body 35 to move in the second cavity 34, that is, the triboelectric nanogenerator 32 and/or the triboelectric nanogenerator 32 can output current in response to the contact and/or impact of the second runout body 35, thereby effectively improving the output performance and the energy conversion efficiency of the nanogenerator module 30.

Embodiment 6

The present embodiment provides an intracardiac energy harvesting device 100 having a size and shape adapted to be implanted into the interior of a heart chamber by an interventional procedure. The intracardiac energy harvesting device 100 comprises a shell 10, a fixing mechanism 20, a nanogenerator module 30, and a power management module 40.

In Embodiment 1, the nanogenerator module 30 comprises a first cavity 31, at least one power generation unit 32, and at least one first runout body 33, wherein the first runout body 33 is configured to move in the first cavity 31 and contact and/or impact the power generation unit 32 in response to the beating of the heart, so that the power generation unit 32 outputs an electrical signal to the power management module 40.

Figure 24:
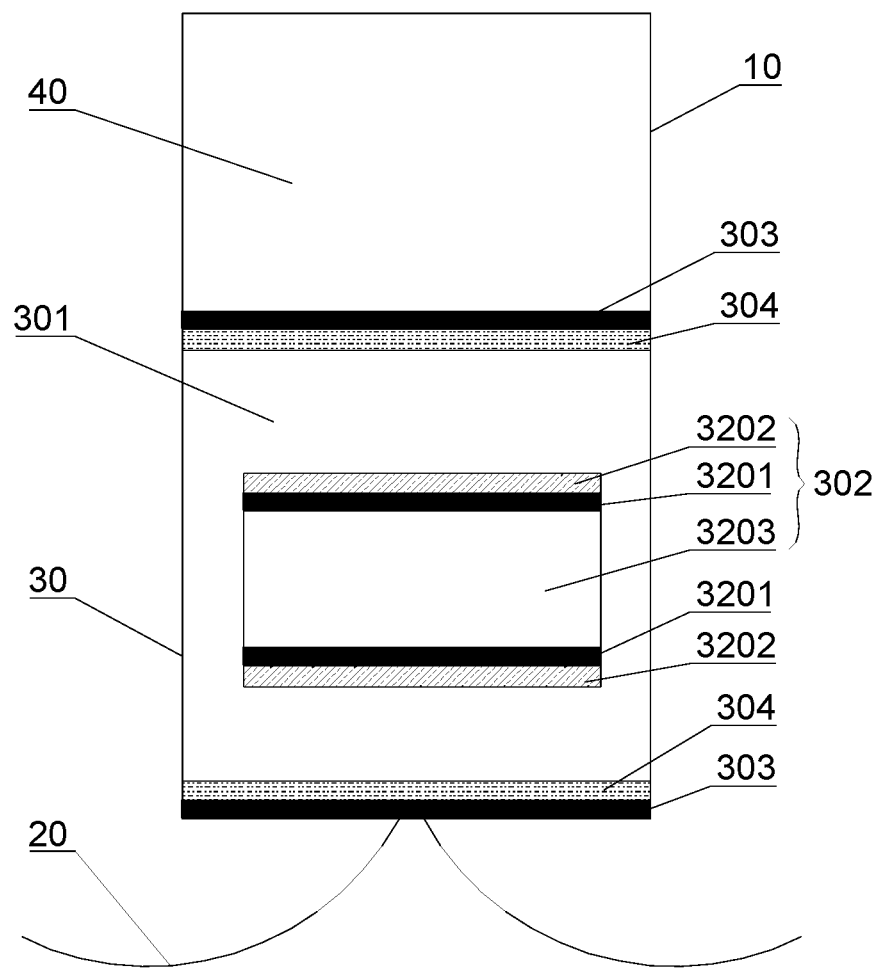
FIG. 24 is a schematic structural diagram of an intracardiac energy harvesting device according to some embodiments.
Figure 25:
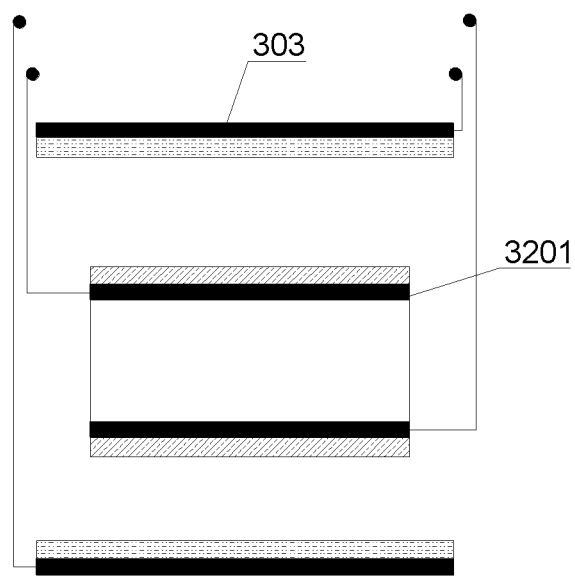
FIG. 25 is a schematic structural diagram of a movable body, a sixth electrode layer, and a sixth friction layer in FIG. 24.
Figure 26:
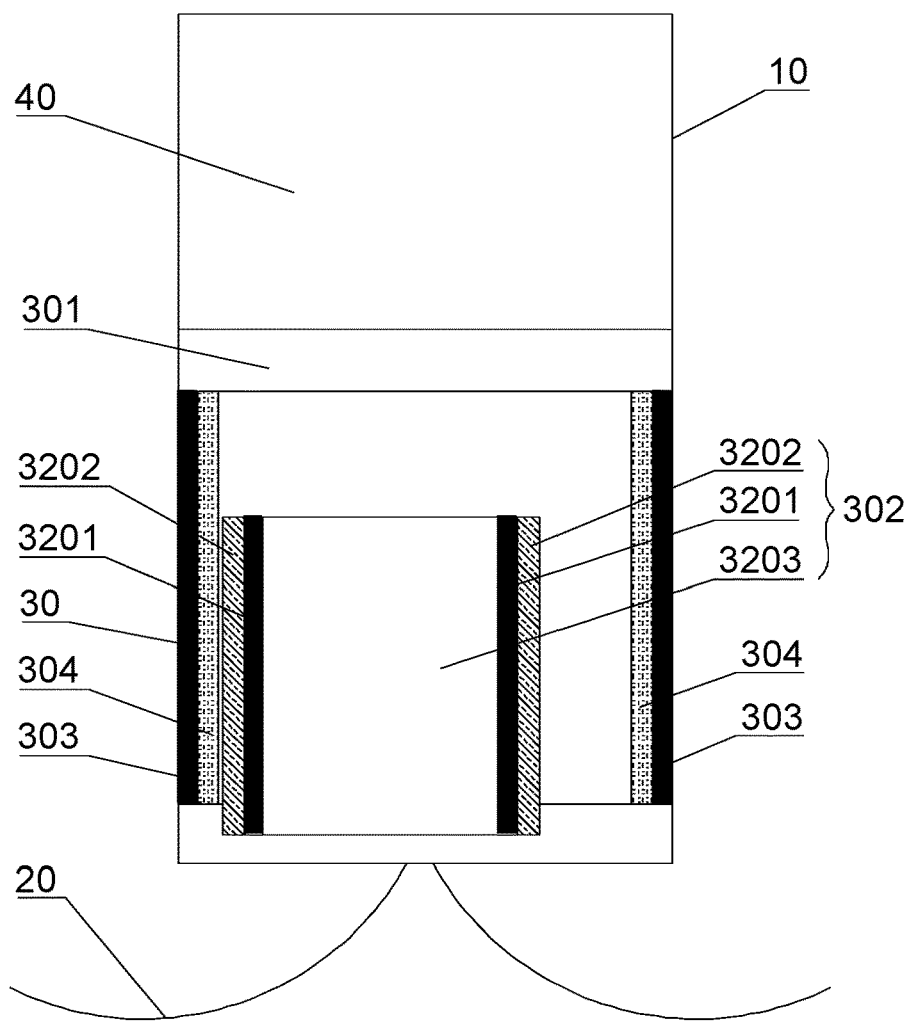
FIG. 26 is a schematic structural diagram of an intracardiac energy harvesting device according to some embodiments.
Figure 27:
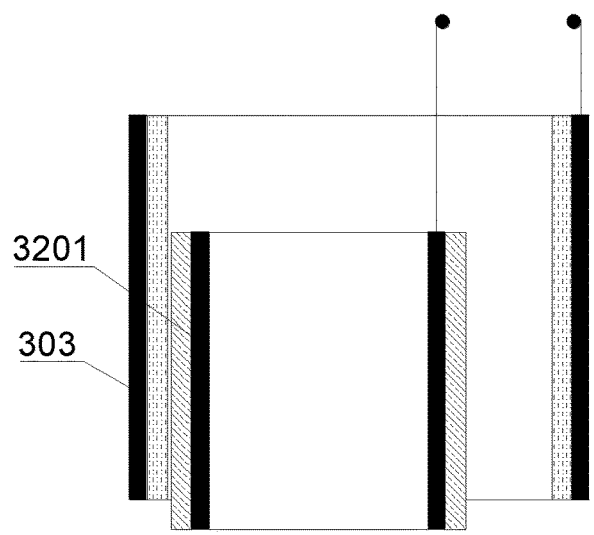
FIG. 27 is a schematic structural diagram of the movable body, the sixth electrode layer, and the sixth friction layer in FIG. 26.

FIG. 24 and FIG. 26 are schematic structural diagrams of an intracardiac energy harvesting device according to some embodiments.

Embodiment 6 differs from Embodiment 1 in that:

Referring to FIGS. 24 and 26, the nanogenerator module 30 includes a third cavity 301, a movable body 302, a sixth electrode layer 303, and a sixth friction layer 304.

The third cavity 301 is a cavity inside the shell 10.

The movable body 302 is movably disposed in the third cavity 301, that is, when the heart beats and drives the shell 10 to move through the fixing mechanism 20, the shell 10 drives the movable body 302 to move in the third cavity 301. The movable body 302 includes a fifth electrode layer 3021, and a fifth friction layer 3022 in contact with the fifth electrode layer 3021, and the fifth friction layer 3022 is disposed on a surface of the fifth electrode layer 3021 close to the sixth friction layer 304. The movable body 302 may further include a core body 3023, so that the fifth electrode layer 3021 is disposed on the core body 3023, and the fifth friction layer 3022 is disposed on the fifth electrode layer 3021.

The sixth electrode layer 303 is disposed in the third cavity 301, and the sixth electrode layer 303 and the fifth electrode layer 3021 are spaced apart from each other. The sixth electrode layer 303 may be disposed on at least one of a top wall, a bottom wall and a side wall of the third cavity 301. FIG. 24 shows an example of a sixth electrode layer 303 disposed on a top wall and a bottom wall of a third cavity 301. FIG. 26 shows an example of a sixth electrode layer 303 disposed on a sidewall of the third cavity 301. The fifth electrode layer 3021 and the sixth electrode layer 303 may be electrically connected to an input electrode of the rectifying unit of the power management module 40 through a fifth wire, respectively. It should be noted that the length of the wire connected to the fifth electrode layer 3021 needs to be appropriate and should not limit the free movement of the movable body 302 in the third cavity 301.

The sixth friction layer 304 is disposed in contact with the sixth electrode layer 303, and the sixth friction layer 304 is disposed on a surface of the sixth electrode layer 303 close to the fifth friction layer 3022.

The movable body 302 is configured to make contact and separation between the fifth friction layer 3022 and the sixth friction layer 304 in response to the beating of the heart, so that the fifth electrode layer 3021 and the sixth electrode layer 303 output electrical signals to the power management module 40.

There is a difference in electronic capacity between the material of the fifth friction layer 3022 and the material of the sixth friction layer 304, so that the surface of the fifth friction layer 3022 and the sixth friction layer 304 can generate contact charges on the surfaces of the fifth friction layer 3022 and the sixth friction layer 304, and the contact surface of one of the fifth friction layer 3022 and the sixth friction layer 304 is positively charged, and the other contact surface is negatively charged.

Each of the material of the fifth friction layer 3022 and the material of the sixth friction layer 304 is selected from a group consisting of an insulator material, a semiconductor material, and a conductor material. The conventional insulating material has triboelectric characteristics and can be used as a material for preparing the fifth friction layer 3022 and the sixth friction layer 304. Relative to the insulator, both the semiconductor and the metal have frictional electrical properties that are prone to loss of electrons, and therefore, the semiconductor and metal can also be used as a material for preparing the fifth and sixth friction layers 3022, 304. In the present embodiment, each of the fifth friction layer 3022 and the sixth friction layer 304 is selected from a group consisting of polyethylene, polypropylene, polystyrene, silica gel, polydimethylsiloxane, polyester, polyurethane, polymethacrylate, polytetrafluoroethylene and nylon, polyimide, nitrile rubber, fluororubber, latex, chitin, cellulose, gold, silver, copper, aluminum, iron and an alloy material, but is not limited thereto.

Each of the material of the fifth electrode layer 3021 and the material of the sixth electrode layer 303 is selected from a group consisting of a metal and a conductive polymer material, wherein the metal is selected from a group consisting of gold, silver, copper, aluminum, iron and an alloy, and the conductive polymer material is selected from a group consisting of carbon nanotubes, graphene and carbon black, but is not limited thereto.

The shell 10 is driven by the fixing mechanism 20 to move, and the shell 10 drives the movable body 302 to move in the third cavity 301 (when the sixth friction layer 304 is disposed along the side wall of the third cavity 301, the fifth friction layer 3022 and the sixth friction layer 304 may be in contact with and separated from each other, and when the sixth friction layer 304 is disposed on the top wall or the bottom wall of the third cavity 301, contact occurs between the fifth friction layer 3022 and the sixth friction layer 304. and so that a potential difference is generated between the fifth electrode layer 3021 and the sixth electrode layer 303 under the coupling of the friction power and the electrostatic induction effect; an alternating electrical signal is generated in the external circuit; along with continuous contraction and relaxation of the heart, the alternating current electric signal continuously generates, so that the fifth electrode layer 3021 and the sixth electrode layer 303 continuously output an electrical signal to the power management module 40.

The shape of the movable body 302 is not limited, for example, the fifth friction layer 3022 and the fifth electrode layer 3021 may be enclosed cylindrical or spherical or non-closed curved surfaces or planes, but are not limited thereto. The shape of the sixth friction layer 304 and the sixth electrode layer 303 is not limited, and the sixth friction layer 304 and the sixth electrode layer 303 may be cylindrical or non-closed curved surfaces or planes enclosed along the inner side wall of the third cavity 301, but are not limited thereto. FIG. 26 shows an example in which the sixth friction layer 304 and the sixth electrode layer 303 enclose a cylindrical shape along the inner side wall of the third cavity 301.

The fifth friction layer 3022 and the sixth friction layer 304 may be prepared by replacing an insulating material or a semiconductor material with a conductor material, that is, the fifth friction layer 3022 may be a conductor material, and instead of the fifth electrode layer 3021 disposed in contact therewith, the sixth friction layer 304 may be a conductor material, and instead of the sixth electrode layer 303 disposed in contact therewith, the conductor material may be selected from at least one of a metal, a conductive oxide, and a conductive polymer material.

At least one of the contact surfaces of the fifth friction layer 3022 and the contact surface of the sixth friction layer 304 is selected from a group consisting of a micro-nano structure, a dot conjugate of the nanomaterial, and a coating of the nanomaterial. The micro-nano structure comprises micro-structures on the order of micron or submicron. The micro-structure is selected from a group consisting of nanowires, nanotubes, nanoparticles, nano-trenches, micro-trenches, nano-cones, micrometer cones, nanospheres, and micro-spherical structures, but is not limited thereto. A contact surface of the fifth friction layer 3022 faces a surface of the sixth friction layer 304, and a contact surface of the sixth friction layer 304 faces a surface of the fifth friction layer 3022.

Embodiment 7

The embodiment of the present invention provides an implantation method of an inner energy harvesting device in a heart. The intracardiac energy harvesting device is any one of the heart internal energy harvesting devices 100 in any one of the above embodiments, and the implantation method of the intracardiac energy harvesting device comprises the following steps.

The intracardiac energy harvesting device 100 is implanted inside the heart chamber through an interventional procedure, for example, the intracardiac energy harvesting device 100 can be implanted into the heart chamber through a catheter, and certainly, the puncture part and the delivery component are not limited thereto.

The intracardiac energy harvesting device 100 is fixed to the heart tissue by means of a fixing mechanism 20 thereof.

Embodiment 8

Figure 28:
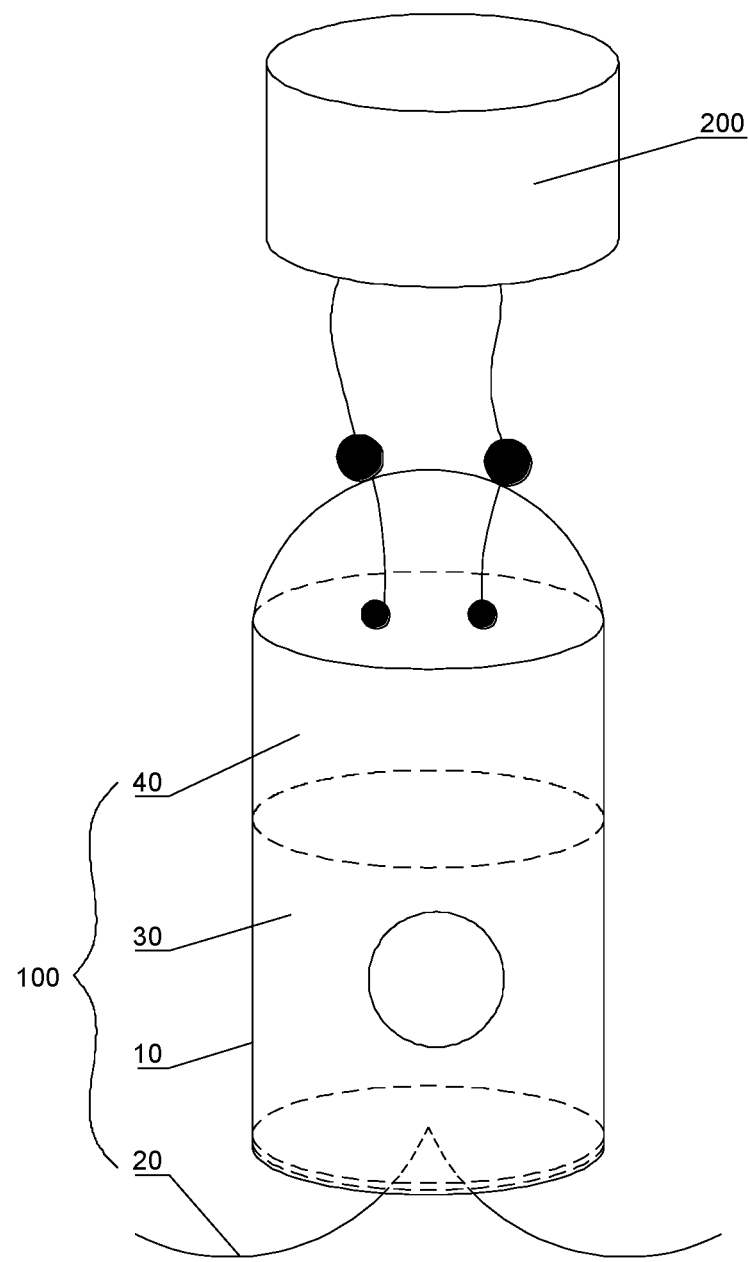
FIG. 28 is a schematic structural diagram of an implantable electronic medical device in accordance with some embodiments.

FIG. 28 is a schematic structural diagram of an implantable electronic medical device, in accordance with some embodiments.

Referring to FIG. 28, the present embodiment provides an implantable electronic medical device. The implantable electronic medical device comprises an intracardiac energy harvesting device 100 and a load function unit 200.

The intracardiac energy harvesting device 100 may be any one of the above embodiments 1-6. The intracardiac energy harvesting device 100 has a size and shape suitable for implantation into the heart chamber by means of an interventional operation.

The intracardiac energy harvesting device 100 is configured to acquire biomechanical energy generated by systolic and diastolic of the heart by means of being fixed inside the heart chamber, and convert it into electrical energy, thereby providing electrical energy for the load function unit 200.

The load function unit 200 is a set functional unit of the implantable electronic medical device, so as to play a role in treating and/or detecting an organism, but the function is not limited thereto. The load function unit is electrically connected with the output end of the power management module 40 of the energy harvesting device in the heart, and the intracardiac energy harvesting device 100 is used for providing electric energy for the load function unit. The load function unit 200 is selected from a group consisting of a functional unit of the leadless cardiac pacemaker, a functional unit of the heart monitoring hemodynamic sensor, and a functional unit of the vascular robot, but is not limited thereto, so long as the electronic medical device which needs to consume electric energy for the treatment, diagnosis or detection of the organism is included in the organism.

Figure 29:
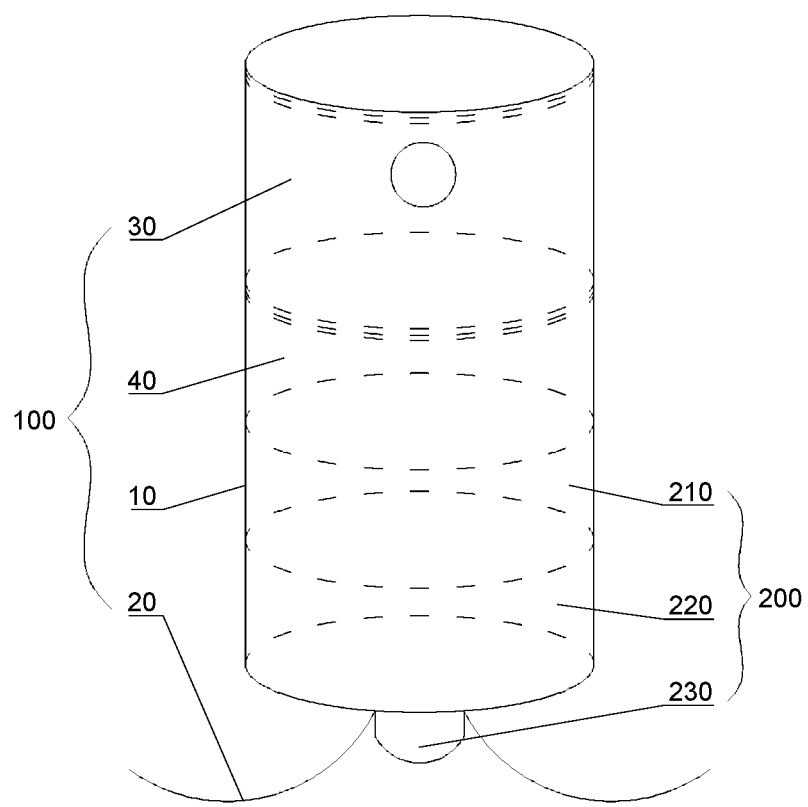
FIG. 29 is a schematic structural diagram of an implantable electronic medical device in accordance with some embodiments.

FIG. 29 is a schematic structural diagram of an implantable electronic medical device in accordance with some embodiments.

Referring to FIG. 29, the load function unit 200 may be integrated with the intracardiac energy harvesting device 100. The integration degree of the implantable electronic medical device is improved, and the volume is reduced.

Figure 30:
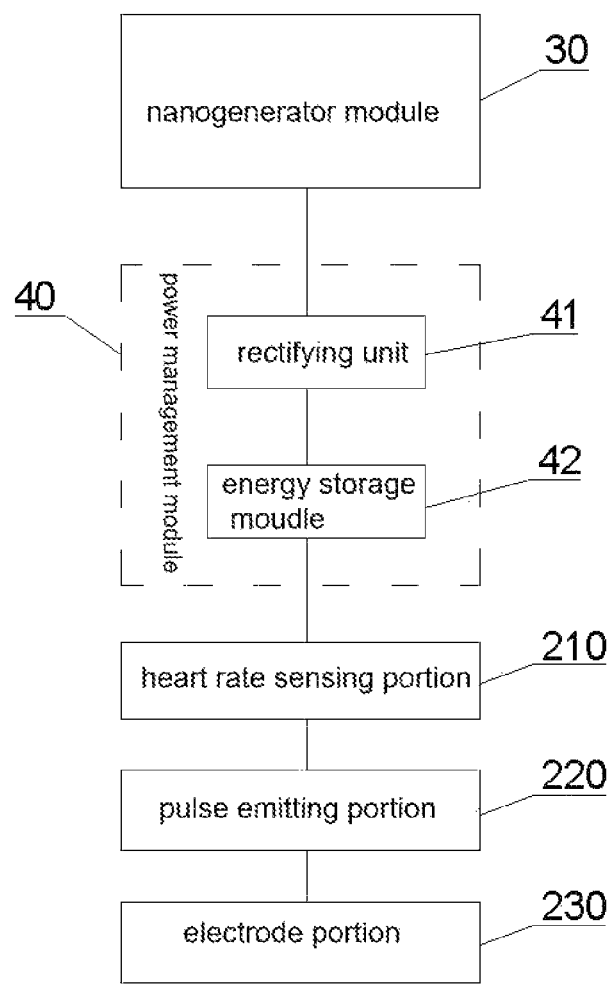
FIG. 30 is a functional block diagram of the implantable electronic medical device of FIG. 29.

FIG. 30 is a functional block diagram of the implantable electronic medical device of FIG. 29.

Referring to FIG. 30, the implantable electronic medical device may be a leadless cardiac pacemaker, and at this time, the load function unit 200 includes a heart rate sensing portion 210, a pulse emitting portion 220, and an electrode portion 230, FIG. 29 illustrates an example of an implantable electronic medical device being a leadless cardiac pacemaker.

The heart rate sensing portion 210 is configured to sense a heart rate, and the heart rate sensing portion 210 may detect the beating state of the heart by means of the electrode portion 230. The heart rate sensing portion 210 may be electrically connected to an output end of the power management module 40 of the intracardiac energy harvesting device 100. The heart rate sensing portion 210 may be disposed inside the shell 10.

The pulse emitting portion 220 is configured to emit an electrical pulse in response to a heart rate sensed by the heart rate sensing portion. The pulse emitting portion 220 may be electrically connected to the heart rate sensing portion 210, and when the heart rate sensing portion 210 senses that the heart rate is low (for example, the heart rate sensing portion 210 perceives that the heart rate is lower than a preset threshold), the pulse emitting portion 220 may generate a pulse current and conduct the pulse current to the heart tissue through the electrode portion 230 to stimulate heart beat. The pulse emitting portion 220 may be disposed inside the shell 10.

The electrode portion 230 is configured to contact the heart tissue to conduct a heart rate sensing signal to the heart rate sensing portion and to conduct an electrical pulse occurring at the pulse emitting portion to the heart. The electrode portion 230 may be electrically connected to the heart rate sensing portion 210 and/or the pulse emitting portion 220. The electrode portion 230 may include two or more electrodes disposed within, on, or near the shell, for example, the electrode portion 230 may include a first electrode and a second electrode, the first electrode and the second electrode may be metal conductors exposed on a sidewall of the shell 10, and the first electrode and the second electrode are insulated from each other on the shell 10. At least one electrode of the electrode portion 230 may be disposed on a portion of the shell 10 close to the fixing mechanism 20, so that when the fixing mechanism 20 fixes the shell 10 on the cardiac tissue, at least one electrode of the electrode portion 230 contacts the heart tissue.

The power management module 40, the heart rate sensing portion 210, the pulse emitting portion 220, and the electrode portion 230 may be sequentially connected by means of a wire or a flexible circuit board, and the portions may be isolated from each other in addition to a wire or a flexible circuit.

The nanogenerator module 30, the power management module 40, the heart rate sensing portion 210, the pulse emitting portion 220, and the electrode portion 230 may be sequentially disposed along the length direction of the shell 10, and the electrode portion 230 may be located at one end close to the fixing mechanism 20, but is not limited thereto. The nanogenerator module 30, the power management module 40, the heart rate sensing portion 210, and the pulse emitting portion 220 may be adjusted in a placement position in the shell 10.

In the overall volume of the shell 10, the volume of the nanogenerator module 30 may account for ⅓, the power management module 40 may occupy a ratio of ⅙, the heart rate sensing portion 210 and the pulse emitting portion 220 may occupy 0.5-2 mm in diameter, and preferably, the diameter of the electrode portion 230 is 0.8 mm.

It can be seen from the above that according to the implantable electronic medical device provided by the embodiment of the present invention, biological mechanical energy generated by cardiac contraction and diastole is collected in the heart chamber through the inner energy harvesting device 100 in the heart, and the mechanical energy is converted into electric energy, so that normal work of the implantable electronic medical device is guaranteed, so that the self-powered implantable electronic medical device is realized, and the technical problem that a bottleneck-battery life of an existing implantable electronic medical device is limited is solved.; the surgical wound is small, damage to the heart is avoided, infection can be effectively avoided, long-term stable power supply can be carried out on the load function unit of the implantable electronic medical device, the technical problem that the existing implantable electronic medical device energy supply technology bottleneck-battery life is limited is solved, the technical problem that the existing implantable electronic medical device energy supply technology bottleneck-battery life is limited is solved, long-term stability can be achieved, and continuous diagnosis and treatment can be achieved through minimally invasive surgery implantation.

The above are only specific embodiments of the present invention, but the scope of protection of the present invention is not limited thereto, and any changes or substitutions which do not involve an inventive effort shall fall within the protection scope of the present invention. Therefore, the protection scope of the present invention should be subject to the protection scope defined in the claims.

What is claimed is:

1. An intracardiac energy harvesting device, comprising:
a shell;
a fixing mechanism arranged on the shell, wherein the fixing mechanism is configured to fix the shell to an interior of a heart chamber to enable the shell to move along with beating of heart;
a nanogenerator module packaged in the shell, wherein the nanogenerator module is configured to output electrical energy in response to movement of the shell as the heart beats; and
a power management module packaged in the shell, wherein the power management module is used for managing an electric energy output by the nanogenerator module;
a first cavity;
at least one power generation unit disposed in the first cavity; and
at least one first runout body, which is freely movable in the first cavity;
wherein the first runout body is configured to contact and/or impact the power generation unit in response to runout of the heart, so that the power generation unit outputs an electrical signal;
the power generation unit is a triboelectric nanogenerator, which comprises: a first friction layer and a second friction layer;
spaces are formed on both sides of the power generation unit, and the spaces on both sides are provided with at least one of the runout bodies; when the first runout body moves, the first friction layer is in contact with and separated from the second friction layer.

2. The intracardiac energy harvesting device, as recited in claim 1, wherein the triboelectric nanogenerator comprises:
a first electrode layer, and the first friction layer disposed in contact with the first electrode layer; and
a second electrode layer, and the second friction layer disposed in contact with the second electrode layer;
wherein the first friction layer and the second friction layer are arranged in a face-to-face manner and are spaced apart by a space for free movement of the first runout body, the first runout body is configured to move between the first friction layer and the second friction layer in response to the runout of the heart, so that the first runout body is in contact with and separated from the first friction layer and is in contact with and separated from the second friction layer, so that the first electrode layer and the second electrode layer output electrical signals to the power management module.

3. The intracardiac energy harvesting device, as recited in claim 1, wherein there is an electron difference between a material of the first friction layer and a material of the second friction layer;
each of the first friction layer and the second friction layer is selected from a group consisting of an insulator material, a semiconductor material, and a conductor material.

4. The intracardiac energy harvesting device, as recited in claim 1, wherein the first friction layer and the second friction layer is a conductor material, and a friction layer of the conductor material replaces an electrode layer disposed in contact therewith.

5. The intracardiac energy harvesting device, as recited in claim 1, wherein at least one of a contact surface of the first friction layer and a contact surface of the second friction layer is selected from a group consisting of a micro-nano structure, a dot conjugate of a nanomaterial, and a coating of a nanomaterial.

6. The intracardiac energy harvesting device, as recited in claim 1, wherein the triboelectric nanogenerator comprises a first substrate, and the first friction layer is disposed on the first substrate; when the first runout body located on one side of the first substrate moves, the first substrate is impacted, so that the first friction layer and the second friction layer are in contact and separated; and/or the triboelectric nanogenerator comprises a second substrate, and the second friction layer is arranged on the second substrate; when the first runout body on one side of the second substrate moves, the second substrate is impacted, so that the first friction layer and the second friction layer are in contact and separated.

7. The intracardiac energy harvesting device, as recited in claim 6, wherein at least one of the first substrate and the second substrate comprises a flexible material to deform due to an impact force of the first runout body and return to an initial state when the impact force of the first runout body is removed; or at least one of the first substrate and the second substrate comprises a flexible material to deform due to an external force, which has an extensibility to extend or retract.

8. The intracardiac energy harvesting device, as recited in claim 7, wherein in a natural state, the first substrate is arc-shaped or arched, and/or the second substrate is arc-shaped or arched.

9. The intracardiac energy harvesting device, as recited in claim 1, wherein the triboelectric nanogenerator comprises a first substrate, and the first friction layer is disposed on the first substrate; the first substrate is fixed on an internal wall of the first cavity; and/or the triboelectric nanogenerator comprises a second substrate, and the second friction layer is arranged on the second substrate; the second substrate is fixed on an internal wall of the first cavity.

10. The intracardiac energy harvesting device, as recited in claim 1, wherein an outer diameter of the first runout body is 100 μm-5 mm.

11. The intracardiac energy harvesting device, as recited in claim 1, wherein an outer surface of the first runout body is selected from a group consisting of a micro-nano structure, a dot conjugate of a nanomaterial, and a coating of a nanomaterial.

12. The intracardiac energy harvesting device, as recited in claim 1, wherein the first runout body is a polyhedron, a sphere or an ellipsoid.

13. The intracardiac energy harvesting device, as recited in claim 1, wherein the intracardiac energy harvesting device has a size and shape adapted to be implanted into the interior of the heart chamber by an interventional procedure.

14. The intracardiac energy harvesting device, as recited in claim 1, wherein an outer diameter of the shell is 5 mm to 15 mm, a length of the shell is 1 cm to 5 cm; a length of the nanogenerator module is 0.5 cm to 4.5 cm.

15. The intracardiac energy harvesting device, as recited in claim 1, wherein the shell is cylindrical.

16. The intracardiac energy harvesting device, as recited in claim 1, wherein the fixing mechanism is disposed at an end or a side portion of the shell.

17. The intracardiac energy harvesting device, as recited in claim 1, wherein the fixing mechanism is selected from a group consisting of a claw-shaped fixing mechanism, a hook-shaped fixing mechanism, a spiral fixing mechanism and a screw fixing mechanism.

18. An implantable electronic medical device, comprising:

the intracardiac energy harvesting device as recited in claim 1; and a load function unit electrically connected with an output end of a power management module of an energy harvesting device in the heart, and the intracardiac energy harvesting device is used for providing electric energy for the load function unit.

19. The implantable electronic medical device, as recited in claim 18, wherein the load function unit is integrated with the intracardiac energy harvesting device.

20. The implantable electronic medical device, as recited in claim 18, wherein the implantable electronic medical device is a leadless cardiac pacemaker, and the load functional unit comprises:

a heart rate sensing unit configured to sense a heart rate;

a pulse emission unit configured to emit an electric pulse in response to the heart rate sensed by the heart rate sensing unit; and an electrode portion configured to contact heart tissue to conduct a heart rate sensing signal to a heart rate sensing portion and conduct an electrical pulse generated by a pulse emitting portion to the heart.

* * * * *